(12) United States Patent  
Goldstein et al.

(10) Patent No.: US 7,348,344 B2  
(45) Date of Patent: Mar. 25, 2008

(54) POLYSUBSTITUTED 1,1-PYRIDYLOXYCYCLOPROPANAMINE COMPOUNDS

(75) Inventors: Solo Goldstein, Suresnes (FR); Claude Guillonneau, Clamart (FR); Yves Charton, Sceaux (FR); Brian Lockhart, Feucherolles (FR); Pierre Lestage, La Celle Saint Cloud (FR)

(73) Assignee: Les Laboratoires Servier, Courbevoie Cedex (FR)

( * ) Notice: Subject to any disclaimer, the term of this patent is extended or adjusted under 35 U.S.C. 154(b) by 0 days.

(21) Appl. No.: 11/493,070

(22) Filed: Jul. 26, 2006

(65) Prior Publication Data

US 2007/0027191 A1 Feb. 1, 2007

(30) Foreign Application Priority Data

Jul. 28, 2005 (FR) .................................. 05 08033

(51) Int. Cl.  
*C07D 213/70* (2006.01)  
*A61K 31/4412* (2006.01)

(52) U.S. Cl. ...................................... 514/345; 546/290
(58) Field of Classification Search ................ 514/345; 546/290  
See application file for complete search history.

(56) References Cited

FOREIGN PATENT DOCUMENTS

EP 1170281 1/2002

OTHER PUBLICATIONS

French Preliminary Search Report for FR05.08033 of Jun. 12, 2006.

*Primary Examiner*—Zinna N. Davis  
(74) *Attorney, Agent, or Firm*—Hueschen and Sage

(57) ABSTRACT

A compound selected from those of formula (I):

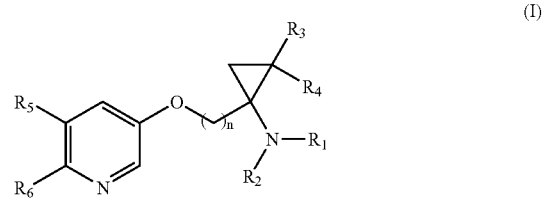

(I)

wherein:
 n represents an integer from 1 to 6 inclusive,
 $R_1$ and $R_2$ represent a hydrogen atom, a $(C_1-C_6)$alkyl group or an aryl-$(C_1-C_6)$alkyl group,
 $R_3$ and $R_4$ represent a hydrogen atom or a $(C_1-C_6)$alkyl group,
 $R_5$ and $R_6$ represent a hydrogen atom, or a $(C_1-C_6)$alkyl, halogen, hydroxy, $(C_1-C_6)$alkoxy, cyano, nitro, $(C_2-C_6)$acyl, $(C_1-C_6)$alkoxycarbonyl, $(C_1-C_6)$trihaloalkyl, $(C_1-C_6)$trihaloalkoxy or optionally substituted amino group,
its enantiomers, diastereoisomers and additional salts thereof with a pharmaceutically acceptable acid or base.

Medicinal products containing the same which are useful in the treatment of conditions requiring a specific nicotinic ligand of α4β2 receptors.

7 Claims, No Drawings

POLYSUBSTITUTED 1,1-PYRIDYLOXYCYCLOPROPANAMINE COMPOUNDS

The present invention relates to new polysubstituted 1,1-pyridyloxycyclopropanamine compounds, to a process for their preparation and to pharmaceutical compositions containing them.

The compounds of the present invention are especially valuable from a pharmacological point of view because of their specific interaction with central nicotinic receptors of type α4β2, having application in the treatment of neuropathologies associated with cerebral ageing, of mood disorders, of pain and of tobacco withdrawal.

Ageing of the population due to increased life expectancy at birth has brought with it a major increase in the incidence of age-related neuropathologies and especially of Alzheimer's disease. The principal clinical manifestations of cerebral ageing and especially of age-related neuropathologies are deficiencies in mnemic and cognitive functions, which may lead to dementia. It has been widely demonstrated that, of the various neuro-transmitters, acetylcholine plays a major role in memory functions and that there is large-scale destruction of the cholinergic neuronal pathways in certain neurodegenerative diseases or when there is inadequate activation in the case of cerebral ageing. For that reason, numerous therapeutic approaches have been aimed at preventing destruction of the neurotransmitter by means of the inhibition of acetylcholinesterase or have sought to provide a substitute for the deficient neurotransmitter. In the latter case, the cholinergic agonists proposed have been of the muscarinic type, which are specific for post-synaptic M1 receptors.

It has recently been shown that the cholinergic impairment associated with Alzheimer's disease affects neurones carrying nicotinic receptors more than those carrying muscarinic receptors (Schroder et al., "Alzheimer disease: therapeutic strategies", Birkhauser Boston, 1994, 181-185). Numerous studies have, moreover, demonstrated that nicotine has memory-facilitating properties (Prog. Neuropsychopharmacol., 1992, 16, 181-191) and that these properties are exerted as much on mnemic functions (Psychopharmacol., 1996, 123, 88-97) as on the faculties of attention and vigilance (Psychopharmacol., 1995, 118, 195-205). Furthermore, nicotine exerts neuroprotective effects with respect to excitotoxic agents such as glutamate (Brain Res., 1994, 644, 181-187).

All of these findings can very probably be linked with epidemiological studies that have shown a lower incidence of Alzheimer's disease and Parkinson's disease in smokers. Furthermore, several studies have shown the value of nicotine in the treatment of mood disorders such as states of depression, anxiety or schizophrenia. Finally, it has been shown that nicotine has antalgic properties. All of the therapeutic properties of nicotine and also those described for other nicotinic agents are based upon activity with respect to central receptors, which differ structurally and pharmacologically from peripheral receptors (muscle and ganglion). The central receptors of type α4β2 are the most represented in the central nervous system and have been implicated in the majority of the therapeutic effects of nicotine (Life Sci., 1995, 56, 545-570).

Several documents such as Synlett., 1999, 7, 1053-1054; J. Med. Chem, 1985, 28(12), 1953-1957 and 1980, 23(3), 339-341; 1970, 13(5), 820-826; 1972, 15(10), 1003-1006; J. Am. Chem. Soc., 1987, 109(13), 4036-4046, or a few patents or patent applications such as DE 36 08 727, EP 124 208 or WO 94/10158 describe and claim compounds containing a 1,1- or 1,2-disubstituted cyclopropane moiety. None of those references describe or suggest that those compounds have pharmacological activity that is specific for nicotinic receptors and, more especially, for central nicotinic receptors of type α4β2, this being a novel property of the compounds described by the Applicant. Patent Application EP 1 170 281 describes 1,1- and 1,2-disubstituted cyclopropane compounds which are nicotinic ligands.

The compounds of the present invention are therefore new and represent powerful selective nicotinic ligands of the central receptor sub-type α4β2. They are consequently of use in the treatment of deficiencies of memory associated with cerebral ageing and with neuro-degenerative diseases such as Alzheimer's disease, Parkinson's disease, Pick's disease, Korsakoff's disease and frontal lobe and subcortical dementias, and also for the treatment of mood disorders, Tourette's syndrome, attention-deficit hyperactivity syndrome, tobacco withdrawal and pain.

More specifically, the present invention relates to compounds of formula (I):

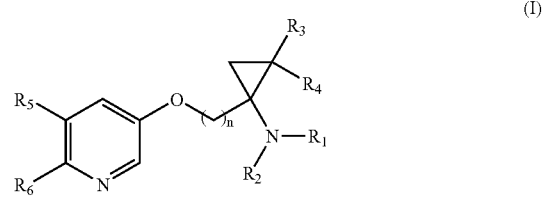

wherein:

n represents an integer of from 1 to 6 inclusive, $R_1$ and $R_2$, which may be identical or different, each independently of the other represent a hydrogen atom, a linear or branched ($C_1$-$C_6$)alkyl group or an aryl-($C_1$-$C_6$)alkyl group in which the alkyl moiety may be linear or branched, $R_3$ and $R_4$, which may be identical or different, each independently of the other represent a hydrogen atom or a linear or branched ($C_1$-$C_6$)alkyl group, wherein at least one of the two groups $R_3$ or $R_4$ represents a linear or branched ($C_1$-$C_6$)alkyl group, $R_5$ and $R_6$, which may be identical or different, each independently of the other represent a hydrogen atom or a linear or branched ($C_1$-$C_6$)alkyl, halogen, hydroxy, linear or branched ($C_1$-$C_6$)alkoxy, cyano, nitro, linear or branched ($C_2$-$C_6$)acyl, linear or branched ($C_1$-$C_6$)alkoxycarbonyl, linear or branched ($C_1$-$C_6$)trihaloalkyl or linear or branched ($C_1$-$C_6$)trihaloalkoxy group or an amino group optionally substituted by one or two linear or branched ($C_1$-$C_6$)alkyl groups, there being understood by aryl group a phenyl, biphenyl, naphthyl, dihydronaphthyl, tetrahydronaphthyl, indanyl or indenyl group, each of those groups being optionally substituted by one or more identical or different groups selected from halogen atoms, linear or branched ($C_1$-$C_6$)alkyl, hydroxy, cyano, nitro, linear or branched ($C_1$-$C_6$)alkoxy, linear or branched ($C_2$-$C_7$)acyl, linear or branched ($C_1$-$C_6$) alkoxycarbonyl, linear or branched ($C_1$-$C_6$)trihaloalkyl and linear or branched ($C_1$-$C_6$)trihaloalkoxy groups and amino groups optionally substituted by one or two linear or branched ($C_1$-$C_6$)alkyl groups.

Preferred compounds of the invention are the compounds wherein n is an integer having the value 1.

The substituents $R_1$ and $R_2$ that are preferred according to the invention are a hydrogen atom and a linear or branched $(C_1-C_6)$alkyl group.

Even more preferably, the substituents $R_1$ and $R_2$ that are preferred according to the invention are a hydrogen atom and a methyl group.

The substituents $R_3$ and $R_4$ that are preferred according to the invention are a hydrogen atom and a methyl group.

The substituents $R_5$ and $R_6$ that are preferred according to the invention are a hydrogen atom and a halogen atom.

Advantageously, preferred compounds of the invention are the compounds wherein $R_5$ represents a halogen atom and $R_6$ represents a hydrogen atom.

Even more advantageously, preferred compounds of the invention are the compounds wherein $R_5$ represents a hydrogen atom and $R_6$ represents a halogen atom.

The notation (1S,2S),(1R,2R) followed by the name of the compound signifies that the product obtained is a racemic mixture and hence that both configurations are possible.

For example:
(1S,2S),(1R,2R)-2-methyl-1-[(3-pyridinyloxy)methyl]cyclopropanamine signifies that the product obtained, a racemic mixture, contains (1S,2S)-2-methyl-1-[(3-pyridinyloxy)-methyl]cyclopropanamine and (1R,2R)-2-ethyl-1-[(3-pyridinyloxy)methyl]cyclopropanamine The notation (R or S) followed by the name of the compound signifies that the product obtained is a an optically pure enantiomer. The presence of (−) and/or (+) indicates the sign of the index of rotation.

The notation (R,S) followed by the name of the compound signifies that the product obtained is a racemic mixture and hence that both configurations are possible.

The notation (1S,2S)- or (1R,2R) followed by the name of the compound signifies that the product obtained is an optically pure enantiomer. The presence of (−) and/or (+) indicates the sign of the index of rotation.

For example:
(1S,2S)- or (1R,2R)-(−)-N,2-dimethyl-1-[(3-pyridinyloxy)methyl]cyclopropanamine dihydrochloride signifies that the product obtained, an optically pure enantiomer, is (1S,2S)-(−)-N,2-dimethyl-1-[(3-pyridinyloxy)methyl]cyclopropanamine dihydrochloride or (1R,2R)-(−)-N,2-dimethyl-1-[(3-pyridinyloxy)methyl]cyclopropanamine dihydrochloride.

The α and β enantiomers are understood to be the optically pure enantiomers of the racemic mixture in question.

In especially advantageous manner, preferred compounds of the invention are:
(1S,2S),(1R,2R)-N,2-dimethyl-1-[(3-pyridinyloxy)methyl]cyclopropanamine
(1S,2S)- or (1R,2R)-(−)-N,2-dimethyl-1-[(3-pyridinyloxy)methyl]cyclopropanamine
(1S,2S)- or (1R,2R)-(+)-N,2-dimethyl-1-[(3-pyridinyloxy)methyl]cyclopropanamine
(1S,2S),(1R,2R)-2-methyl-1-[(3-pyridinyloxy)methyl]cyclopropanamine
(1S,2S)- or (1R,2R)-(−)-2-methyl-1-[(3-pyridinyloxy)methyl]cyclopropanamine
(1S,2S)- or (1R,2R)-(+)-2-methyl 1-[(3-pyridinyloxy)methyl]cyclopropanamine
(1S,2S),(1R,2R)-N,N,2-trimethyl-1-[(3-pyridinyloxy)methyl]cyclopropanamine
(1S,2S)- or (1R,2R)-(+)-N,N,2-trimethyl 1-[(3-pyridinyloxy)methyl]cyclopropanamine
(1S,2S)- or (1R,2R)-(−)-N,N,2-trimethyl-1-[(3-pyridinyloxy)methyl]cyclopropanamine
(1S,2S),(1R,2R)-1-{[(6-chloro-3-pyridinyl)oxy]methyl}-N,2-dimethylcyclopropanamine
(1S,2S)- or (1R,2R)-(−)-1-{[(6-chloro-3-pyridinyl)oxy]methyl}-N,2-dimethylcyclopropanamine
(1S,2S)- or (1R,2R)-(+)-1-{[(6-chloro-3-pyridinyl)oxy]methyl}-N,2-dimethylcyclopropanamine
(1S,2S),(1R,2R)-1-{[(6-chloro-3-pyridinyl)oxy]methyl}-2-methylcyclopropanamine
(1S,2S)- or (1R,2R)-(−)-1-{[(6-chloro-3-pyridinyl)oxy]methyl-}2-methylcyclopropanamine
(1S,2S)- or (1R,2R)-(+)-1-{[(6-chloro-3-pyridinyl)oxy]methyl}-2-methylcyclopropanamine
(1S,2S),(1R,2R)-1-{[(6-chloro-3-pyridinyl)oxy]methyl-}-N,N,2-trimethylcyclopropanamine
(1S,2S)- or (1R,2R)-(+)-1-{[(6-chloro-3-pyridinyl)oxy]methyl}-N,N,2-trimethylcyclopropanamine
(1S,2S)- or (1R,2R)-(−)-1-{[(6-chloro-3-pyridinyl)oxy]methyl}-N,N,2-trimethylcyclopropanamine
(1S,2R), (1R,2S)-N,2-dimethyl-1-[(3-pyridinyloxy)methyl]cyclopropanamine
(1S,2R)- or (1R,2S)-(+)-N,2-dimethyl-1-[(3-pyridinyloxy)methyl]cyclopropanamine
(1S,2R)- or (1R,2S)-(−)-N,2-dimethyl-1-[(3-pyridinyloxy)methyl]cyclopropanamine
(1S,2R), (1R,2S)-1-{[(5-bromo-3-pyridinyl)oxy]methyl}-N,2-dimethylcyclopropanamine
(1S,2R), (1R,2S)-2-methyl-1-[(3-pyridinyloxy)methyl]cyclopropanamine
(1S,2R), (1R,2S)-N,N,2-trimethyl-1-[(3-pyridinyloxy)methyl]cyclopropanamine
(R,S)-N,2,2-trimethyl-1-[(3-pyridinyloxy)methyl]cyclopropanamine
(R or S)-(+)-N,2,2-trimethyl-1-[(3-pyridinyloxy)methyl]cyclopropanamine
(R or S)-(−)-N,2,2-trimethyl-1-[(3-pyridinyloxy)methyl]cyclopropanamine The isomers, as well as the addition salts with a pharmaceutically acceptable acid or base, of the preferred compounds form an integral part of the invention.

Among the pharmaceutically acceptable acids there may be mentioned, without implying any limitation, hydrochloric acid, hydrobromic acid, sulphuric acid, phosphonic acid, acetic acid, trifluoroacetic acid, lactic acid, pyruvic acid, malonic acid, succinic acid, glutaric acid, fumaric acid, tartaric acid, maleic acid, citric acid, ascorbic acid, oxalic acid, methanesulphonic acid, camphoric acid etc.

Among the pharmaceutically acceptable bases there may be mentioned, without implying any limitation, sodium hydroxide, potassium hydroxide, triethylamine, tert-butylamine etc.

The present invention relates also to a process for the preparation of compounds of formula (I), which is characterised in that there is used as starting material a compound of formula (II):

$$\underset{R'}{\overset{H}{\diagup}}C=C\underset{R}{\overset{(CH_2)_{n-1}-COOEt,}{\diagdown}} \quad (II)$$

wherein R represents a group selected from ethoxycarbonyl, cyano and isocyano and R' represents a group selected from methyl and 2-bromopropyl, which compound of formula (II)

is reacted with trimethylsulphoxonium iodide in the presence of sodium hydride in dimethyl sulphoxide to yield compounds of formula (III):

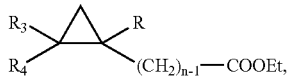
(III)

wherein R is as defined hereinabove and $R_3$, $R_4$ and n are as defined for formula (I), which compounds of formula (III) are:
  either, when R represents an ethoxycarbonyl group, placed in the presence of sodium hydroxide in ethanol to yield compounds of formula (IV):

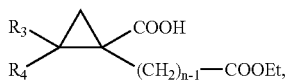
(IV)

wherein $R_3$, $R_4$ and n are as defined hereinabove, which compounds of formula (IV) are reacted with diphenylphosphoryl azide and tert-butanol in toluene, in the presence of triethylamine, to yield compounds of formula (V):

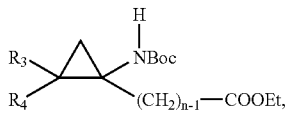
(V)

wherein $R_3$, $R_4$ and n are as defined hereinabove and Boc represents a tert-butoxycarbonyl group, which compounds of formula (V) are reacted with a compound of formula (VI):

(VI), wherein $R'_1$ represents a group selected from linear or branched $(C_1-C_6)$alkyl and aryl-$(C_1-C_6)$alkyl in which the alkyl moiety may be linear or branched and $L_1$ represents a leaving group customary in organic chemistry, in the presence of potassium tert-butanolate in dimethylformamide, to yield compounds of formula (VII):

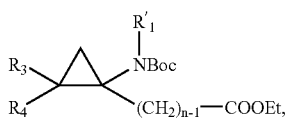
(VII)

wherein $R_3$, $R_4$, $R'_1$, Boc and n are as defined hereinabove, the totality of the compounds of formula (V) and (VII) constituting the compounds of formula (VIII)

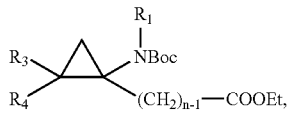
(VIII)

wherein $R_3$, $R_4$, Boc and n are as defined hereinabove and $R_1$ is as defined for formula (I), which compounds of formula (VIII) are:
  either placed in the presence of a reducing agent in an anhydrous solvent to yield compounds of formula (IX):

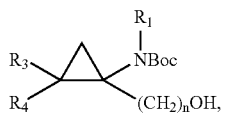
(IX)

wherein $R_3$, $R_4$, Boc, n and $R_1$ are as defined hereinabove, which compounds of formula (IX) are either reacted with triphenylphosphine and tetrabromomethane in ether to yield compounds of formula (X):

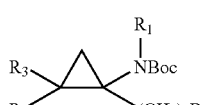
(X)

wherein $R_3$, $R_4$, Boc, n and $R_1$ are as defined hereinabove, which compounds of formula (X) are reacted with a compound of formula (XI):

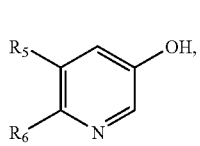
(XI)

wherein $R_5$ and $R_6$ are as defined for formula (I), in the presence of caesium carbonate in butanone, to yield compounds of formula (XII):

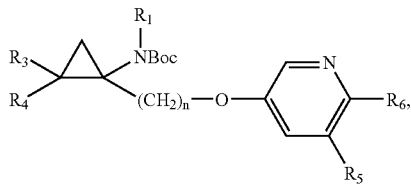
(XII)

wherein $R_3$, $R_4$, $R_5$, $R_6$, $R_1$, n and Boc are as defined hereinabove, which compounds of formula (XII) are placed in the presence of hydrochloric acid in dioxane to yield compounds of formula (I/a), a particular case of the compounds of formula (I):

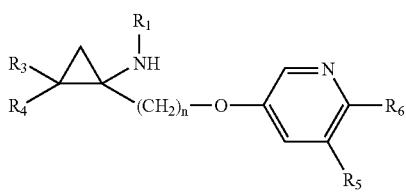
(I/a)

wherein $R_1$, $R_3$, $R_4$, $R_5$, $R_6$ and n are as defined hereinabove, which compounds of formula (I/a) are:
either treated with formic acid and an aqueous formaldehyde solution to yield compounds of formula (I/b), a particular case of the compounds of formula (I):

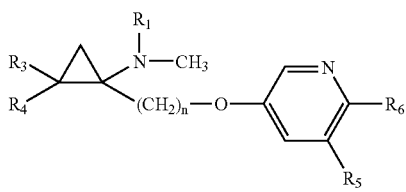
(I/b)

wherein $R_1$, $R_3$, $R_4$, $R_5$, $R_6$ and n are as defined hereinabove, or reacted with a compound of formula (XIII):

R'$_2$-L$_1$  (III), wherein $L_1$ is as defined hereinabove and R'$_2$ represents a group selected from linear or branched ($C_1$-$C_6$)alkyl and aryl-($C_1$-$C_6$)alkyl in which the alkyl moiety may be linear or branched, under the same conditions as the compounds of formula (V), to yield compounds of formula (I/c), a particular case of the compounds of formula (I):

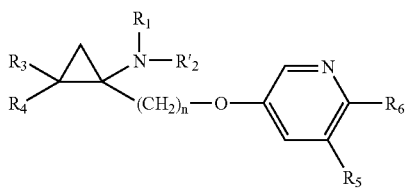
(I/c)

wherein $R_1$, $R_3$, $R_4$, $R_5$, $R_6$, n and $R_{12}$ are as defined hereinabove, or which compounds of formula (VIII) are:
either treated with formic acid and an aqueous formaldehyde solution to yield compounds of formula (XIV):

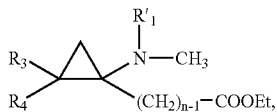
(XIV)

wherein R'$_1$, $R_3$, $R_4$ and n are as defined hereinabove, or treated, in succession,:

with hydrochloric acid in dioxane
and then with a compound of formula (XIII) as defined hereinabove, under the same conditions as compounds of formula (V), to yield compounds of formula (XV):

(XV)

wherein R', R'$_2$, $R_3$, $R_4$ and n are as defined hereinabove, which compounds of formula (XIV) and (XV) are placed in the presence of a reducing agent in an anhydrous solvent to yield compounds of formula (XVI):

(XVI)

R$_3$\
R$_4$/△\N—R'$_2$
         |
         R'$_1$
(CH$_2$)$_n$—OH, wherein R'$_1$, R'$_2$, $R_3$, $R_4$ and n are as defined hereinabove, which compounds of formula (XVI) are reacted with a compound of formula (XVII):

(XVII)

R$_5$\_/\_Hal,
R$_6$—N wherein $R_5$ and $R_6$ are as defined hereinabove and Hal represents a bromine or fluorine atom, in the presence of potassium tert-butanolate in DMSO, to yield compounds of formula (I/d), a particular case of the compounds of formula (I):

(I/d)

wherein R'$_1$, R'$_2$, $R_3$, $R_4$, $R_5$, $R_6$ and n are as defined hereinabove, which compounds of formula (I/d), when R'$_1$ represents a benzyl group, are reacted with hydrochloric acid in the presence of palladium hydroxide in ethanol to yield compounds of formula (I/e), a particular case of the compounds of formula (I):

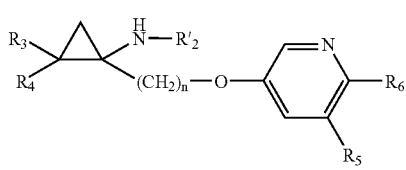 (I/e)

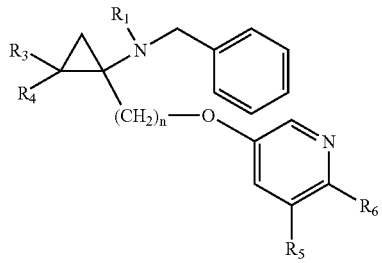 (I/f)

wherein $R'_2$, $R_3$, $R_4$, $R_5$, $R_6$ and n are as defined hereinabove, or which compounds of formula (VIII) are:
treated, in succession,
with hydrochloric acid in ethanol,
and then with aqueous sodium hydrogen carbonate solution, to yield compounds of formula (XVIII):

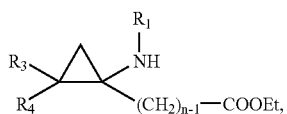 (XVIII)

wherein $R_1$, $R_3$, $R_4'$ and n are as defined hereinabove, which compounds of formula (XVIII) are reacted with benzoyl chloride, in the presence of triethylamine in tetrahydrofuran, to yield compounds of formula (XIX):

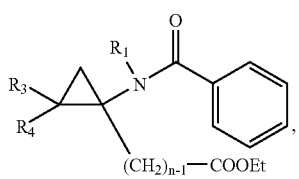 (XIX)

wherein $R_1$, $R_3$, $R_4$ and n are as defined hereinabove, which compounds of formula (XIX) are placed in the presence of a reducing agent in an anhydrous solvent to yield compounds of formula (XX):

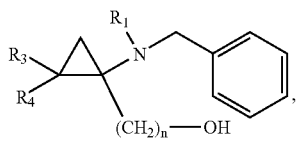 (XX)

wherein $R_1$, $R_3$, $R_4$ and n are as defined hereinabove, which compounds of formula (XX) are subjected to the same reaction conditions as the compounds of formula (XVI) to yield compounds of formula (I/f), a particular case of the compounds of formula (I):

wherein $R_1$, $R_3$, $R_4$, $R_5$, $R_6$ and n are as defined hereinabove, which compounds of formula (I/f) are subjected to the same reactions conditions as the compounds of formula (I/d) to yield compounds of formula (I/a) as defined hereinabove, a particular case of the compounds of formula (I), or which compounds of formula (IX) are:
when $R_1$ represents a hydrogen atom, reacted with hydrochloric acid in dioxane to yield compounds of formula (XXI):

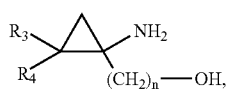 (XXI)

wherein $R_3$, $R_4$ and n are as defined hereinabove, which compounds of formula (XXI) are subjected to the same reactions conditions as the compounds of formula (XVI) to yield compounds of formula (I/g), a particular case of the compounds of formula (I), the compounds of formula (I/g) having cis stereochemistry of $(CH_2)_n$ in relation to one of the substituents $R_3$ or $R_4$, which represents an alkyl radical, while the other substituent $R_3$ or $R_4$ represents a hydrogen atom:

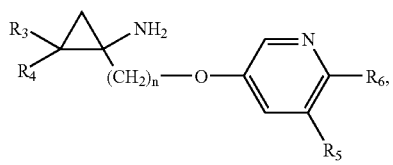 (I/g)

wherein $R_3$, $R_4$, $R_5$, $R_6$ and n are as defined hereinabove, or which compounds of formula (III) are:
either, when R represents an isocyano group, reacted with lithium aluminium hydride in ether to yield compounds of formula (XXII):

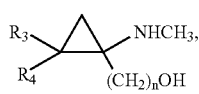 (XXII)

wherein $R_3$, $R_4$ and n are as defined hereinabove, which compounds of formula (XXII) are reacted with a compound of formula (XVII) as defined hereinabove, under the same conditions as the compounds of formula (XVI), to yield compounds of formula (I/h), a particular case of the compounds of formula (I):

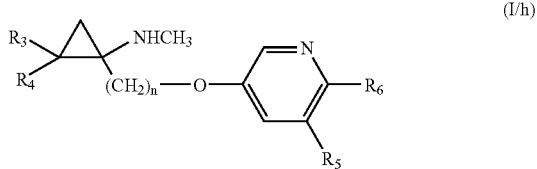

(I/h)

wherein $R_3$, $R_4$, $R_5$, $R_6$ and n are as defined hereinabove, or, when R represents a cyano group, reacted with sodium borohydride in tetrahydrofuran to yield compounds of formula (XXIII):

(XXIII)

wherein $R_3$, $R_4$ and n are as defined hereinabove, which compounds of formula (XXIII) are subjected to the same reaction conditions as the compounds of formula (XVI) to yield compounds of formula (XXIV)

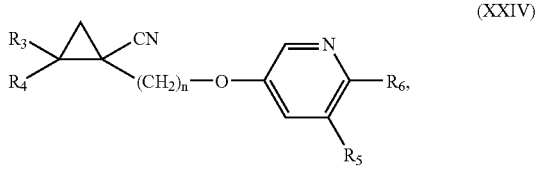

(XXIV)

wherein $R_3$, $R_4$, $R_5$, $R_6$ and n are as defined hereinabove, which compounds of formula (XXIV) are placed in the presence of an aqueous solution of hydrogen peroxide and lithium hydroxide in ethanol to yield compounds of formula (XXV):

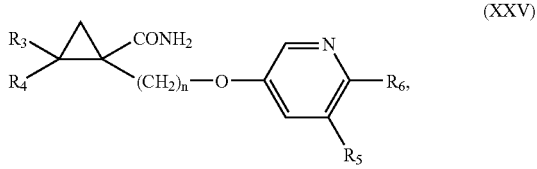

(XXV)

wherein $R_3$, $R_4$, $R_5$, $R_6$ and n are as defined hereinabove, which compounds of formula (XXV) are reacted with bromine and potassium hydroxide in water to yield compounds of formula (I/i), a particular case of the compounds of formula (I), the compounds of formula (I/i) having cis stereochemistry of $NH_2$ in relation to one of the substituents $R_3$ or $R_4$, which represents an alkyl radical, while the other substituent $R_3$ or $R_4$ represents a hydrogen atom:

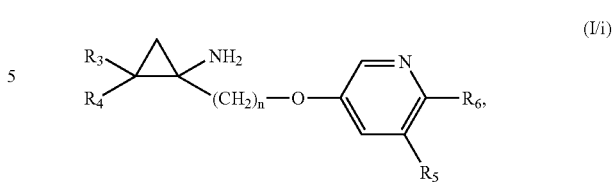

(I/i)

wherein $R_3$, $R_4$, $R_5$, $R_6$ and n are as defined hereinabove, which compounds of formula (I/i) are subjected to the same reactions conditions as the compounds of formula (I/a) to yield compounds of formula (I/j), a particular case of the compounds of formula (I):

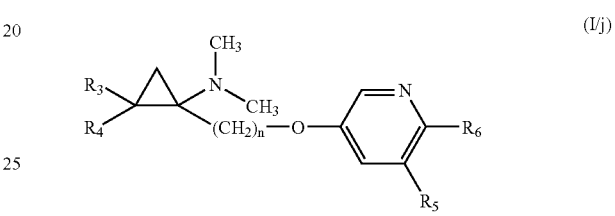

(I/j)

wherein $R_3$, $R_4$, $R_5$, R and n are as defined hereinabove, the totality of the compounds of formula (I/a) to (I/j) constituting the totality of the compounds of the invention, which are purified, where appropriate, according to conventional purification techniques, which may be separated into their different isomers according to a conventional separation technique, and which are converted, where appropriate, into addition salts thereof with a pharmaceutically acceptable acid or base.

The compounds of formulae (II), (VI), (XI), (XIII) and (XVII) are either commercial products or are obtained according to conventional methods of organic synthesis well known to the person skilled in the art.

According to one embodiment of the invention, in the case where one of the substituents $R_3$ or $R_4$ represents a linear or branched ($C_1$-$C_6$)alkyl and the other substituent $R_3$ or $R_4$ represents a hydrogen atom, compounds of formula (I) with cis stereochemistry of $(CH_2)_n$ in relation to the substituent $R_3$ or $R_4$, which represents an alkyl radical, of formula (I/$_1$):

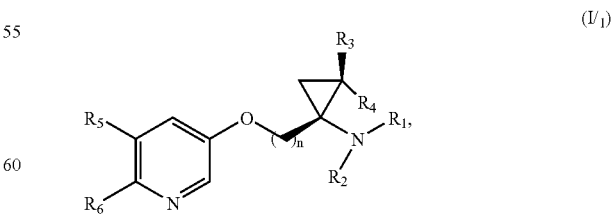

(I/$_1$)

wherein $R_3$ represents a linear or branched ($C_1$-$C_6$)alkyl group, $R_4$ represents a hydrogen atom and $R_1$, $R_2$, $R_5$, $R_6$ and n are as defined for formula (I), can be prepared starting from a compound of formula (III/$_1$):

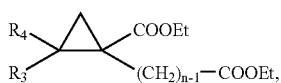
(III/$_1$)

wherein $R_3$, $R_4$ and n are as defined hereinabove, which is placed in the presence of sodium hydroxide in ethanol to yield compounds of formula (IV/$_1$):

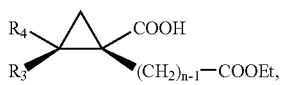
(IV/$_1$)

wherein $R_3$, $R_4$ and n are as defined hereinabove, which compounds of formula (IV/$_1$) are reacted with diphenylphosphoryl azide and tert-butanol in toluene, in the presence of triethylamine, to yield compounds of formula (V/$_1$):

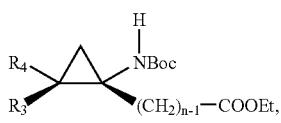
(V/$_1$)

wherein $R_3$, $R_4$, n et Boc are as defined hereinabove, which compounds of formula (V/$_1$) are reacted with a compound of formula (VI) as defined hereinabove, in the presence of potassium tert-butanolate in dimethylformamide, to yield compounds of formula (VI/$_1$):

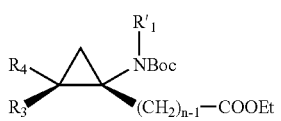
(VI/$_1$)

wherein $R_3$, $R_4$, n, $R'_1$, et Boc are as defined hereinabove, the totality of the compounds of formulae (V/$_1$) and (VI/$_1$) constituting the compounds of formula (VII/$_1$)

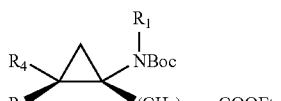
(VII/$_1$)

wherein $R_1$, $R_3$, $R_4$, n et Boc are as defined hereinabove, which compounds of formula (VII/$_1$) are:
either treated with formic acid and an aqueous formaldehyde solution, to yield compounds of formula (VIII/$_1$)

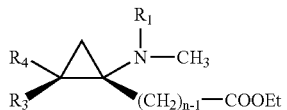
(VIII/$_1$)

wherein $R_1$, $R_3$, $R_4$ and n are as defined hereinabove,
or treated in succession with hydrochloric acid in dioxane then with a compound of formula (XIII), as defined hereinabove, in the presence of potassium tert-butanolate in dimethylformamide, to yield compounds of formula (IX/$_1$):

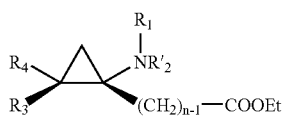
(IX/$_1$)

wherein $R_1$, $R_3$, $R_4$, n and $R'_2$ are as defined hereinabove, which compounds of formulae (VII/$_1$), (VIII/$_1$) and (IX/$_1$) are placed in the presence of a reducing agent in an anhydrous solvent, to yield compounds of formula (X/$_1$):

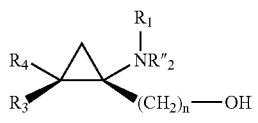
(X/$_1$)

wherein $R''_2$ represents a Boc or $CH_3$ group and $R'_{12}$ and $R_1$, $R_3$, $R_4$ and n are as defined hereinabove, which compounds of formula (X/$_1$) are:
either, when $R''_2$ represents a Boc group, placed in the presence of hydrochloric acid in dioxane to yield compounds of formula (XI/$_1$)

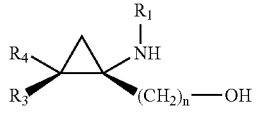
(XI/$_1$)

wherein $R_1$, $R_3$, $R_4$ and n are as defined hereinabove, the compounds of formulae (X/$_1$) and (XI/$_1$) constituting the compounds of formula (XII/$_1$):

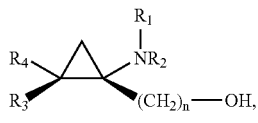
(XII/$_1$)

wherein $R_1$, $R_2$, $R_3$, $R_4$ and n are as defined hereinabove, which compounds of formula (XII/$_1$) are reacted with compounds of formula (XVII), as defined hereinabove, in the presence of potassium tert-butanolate in DMSO, to yield compounds of formula (I/a$_1$), a particular case of the compounds of formula (I):

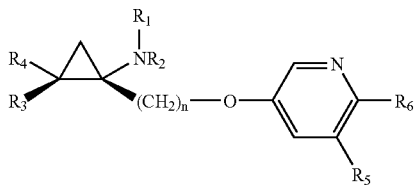

(I/a$_1$)

wherein R$_1$, R$_2$, R$_3$, R$_4$, R$_5$, R$_6$ and n are as defined hereinabove, and the compounds of formula (I/a$_1$) are purified by chiral HPLC and then converted to salts using an ethanolic solution of hydrochloric acid to obtain the chlorinated salts of the two corresponding (−) and (+) isomers, or placed in the presence of triphenylphosphine and tetrabromomethane in ether to yield compounds of formula (XIII/$_1$):

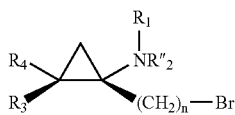

(XIII/$_1$)

wherein R$_1$, R$_3$, R$_4$, R″$_2$ and n are as defined hereinabove, which compounds of formula (XIII/$_1$) are reacted with the compound of formula (XI), as defined hereinabove, in the presence of caesium carbonate in butanone, to yield compounds of formula (XIV/$_1$):

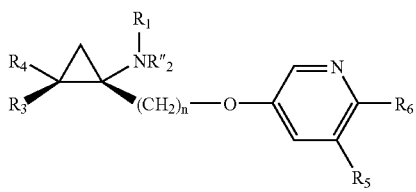

(XIV/$_1$)

wherein R$_1$, R$_3$, R$_4$, R$_5$, R$_6$, R″$_2$ and n are as defined hereinabove, which compounds of formula (XIV/$_1$), when R″$_2$ represents a Boc group, are placed in the presence of hydrochloric acid in dioxane to yield compounds of formula (I/b$_1$), a particular case of the compounds of formula (I):

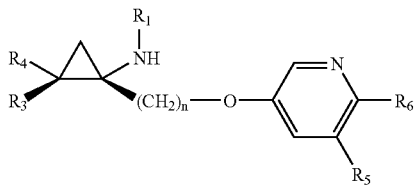

(I/b$_1$)

wherein R$_1$, R$_3$, R$_4$, R$_5$, R$_6$ and n are as defined hereinabove, and the compounds of formula (I/b$_1$) are purified under the same conditions as the compounds of formula (I/a$_1$), it being possible for the compounds of formulae (I/a$_1$) and (I/b$_1$), when R$_1$ and/or R$_2$ represent a hydrogen atom, optionally to be treated, prior to purification, with formic acid and an aqueous formaldehyde solution to yield compounds of formulae (I/c$_1$), (I/c'$_1$) and (I/c″$_1$), particular cases of the compounds of formula (I):

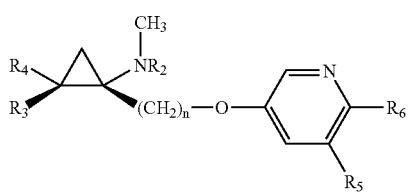

(I/c$_1$)

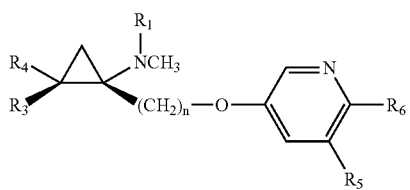

(I/c'$_1$)

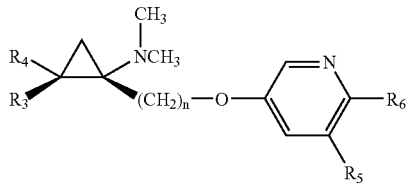

(I/c″$_1$)

wherein R$_1$, R$_2$, R$_3$, R$_4$, R$_5$, R$_6$ and n are as defined hereinabove, which compounds of formulae (I/c$_1$), (I/c'$_1$) and (I/c″$_1$) are purified under the same conditions as the compounds of formula (I/a$_1$).

According to another embodiment of the invention, in the case where one of the substituents R$_3$ or R$_4$ represents a linear or branched (C$_1$-C$_6$)alkyl and the other substituent R$_3$ or R$_4$ represents a hydrogen atom, the compounds of formula (I) with cis stereochemistry of NR$_1$R$_2$ in relation to the substituent R$_3$ or R$_4$, which represents an alkyl radical, of formula (I/$_2$):

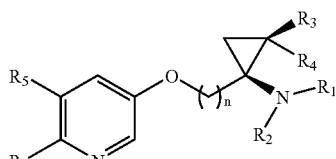

(I/$_2$)

wherein R$_3$ represents a linear or branched (C$_1$-C$_6$)alkyl group, R$_4$ represents a hydrogen atom and R$_1$, R$_2$, R$_5$, R$_6$ and n are as defined for formula (I), can be prepared starting from a compound of formula (II/$_2$):

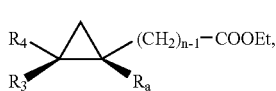

(II/$_2$)

wherein $R_a$ represents a cyano or isocyano group and $R_3$, $R_4$ and n are as defined hereinabove, which:
either, when $R_a$ represents an isocyano group, is placed in the presence of a reducing agent in an anhydrous solvent to yield compounds of formula (III/$_2$):

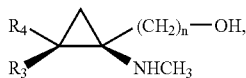

(III/$_2$)

wherein $R_3$, $R_4$ and n are as defined hereinabove, which compounds of formula (III/$_2$) are reacted with a compound of formula (XVII), as defined hereinabove, in the presence of a strong base in an anhydrous solvent, to yield compounds of formula (I/a$_2$), a particular case of the compounds of formula (I):

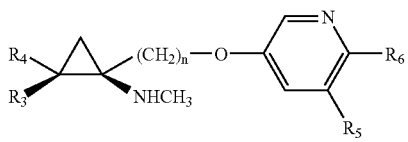

(I/a$_2$)

wherein $R_3$, $R_4$, $R_5$, $R_6$ and n are as defined hereinabove,
or, when $R_a$ represents a cyano group, is placed in the presence of sodium borohydride in a water/tetrahydrofuran mixture to yield compounds of formula (IV/$_2$):

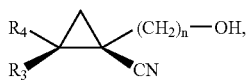

(IV/$_2$)

wherein $R_3$, $R_4$ and n are as defined hereinabove, which compounds of formula (IV/$_2$) are reacted with a compound of formula (XVII), as defined hereinabove, in the presence of a strong base in an anhydrous solvent, to yield compounds of formula (V/$_2$):

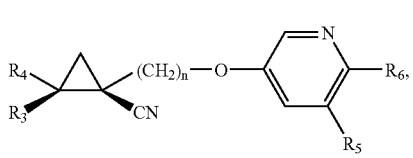

(V/$_2$)

wherein $R_3$, $R_4$, $R_5$, $R_6$ and n are as defined hereinabove, which compounds of formula (V/$_2$) are placed in the presence of lithium hydroxide and hydrogen peroxide in ethanol to yield compounds of formula (VI/$_2$):

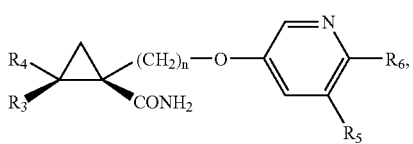

(VI/$_2$)

wherein $R_3$, $R_4$, $R_5$, $R_6$ and n are as defined hereinabove, which compounds of formula (VI/$_2$) are placed in the presence of potassium hydroxide and bromine in water to yield compounds of formula (I/b$_2$), particular cases of the compounds of formula (I):

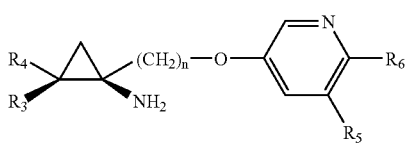

(I/b$_2$)

wherein $R_3$, $R_4$, $R_5$, $R_6$ and n are as defined hereinabove, and the compounds of formula (I/a$_2$) and (I/b$_2$) are purified under the same conditions as the compounds of formula (I/a$_1$):

it being possible, prior to purification, for the compounds of formulae (I/a$_2$) and (I/b$_2$) optionally to be treated under the same conditions as the compounds of formulae (I/c$_1$), (I/c'$_1$) and (I/c"$_1$) to yield compounds of formula (I/c$_2$), a particular case of the compounds of formula (I):

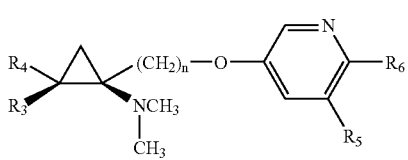

(I/c$_2$)

wherein $R_3$, $R_4$, $R_5$, $R_6$ and n are as defined hereinabove, and the compounds of formula (I/c$_2$) are purified under the same conditions as the compounds of formula (I/a$_1$).

Generally, isomers of the compounds of the invention are understood to be optical isomers such as enantiomers and diastereoisomers. More especially, pure enantiomeric forms of the compounds of the invention may be separated by starting from mixtures of enantiomers which are reacted with a racemate-separating agent that can be released, the said agent being itself in the form a pure enantiomer, which allows the corresponding diastereoisomers to be obtained. The diastereoisomers are then separated according to separation techniques well known to the person skilled in the art, such as crystallisation or chromatography, and the separating agent is then removed using conventional techniques of organic chemistry, resulting in a pure enantiomer being obtained.

The compounds of the invention that are present in the form of a mixture of diastereoisomers are isolated in a pure form by using conventional separation techniques such as chromatography.

In certain particular cases, the process for the preparation of compounds of the invention may result in the predominant formation of one enantiomer or diastereoisomer over the other.

By virtue of their pharmacological properties as nicotinic ligands, and their selectivity for the receptor sub-type α4β2, the compounds of the present invention are of use in the treatment of deficiencies of memory associated with cerebral ageing and neurodegenerative diseases such as Alzheimer's disease, Parkinson's disease, Pick's disease, Korsakoff's disease and frontal lobe and subcortical dementias, and also for the treatment of mood disorders, Tourette's syndrome, attention-deficit hyperactivity syndrome, tobacco withdrawal and pain.

The present invention relates also to pharmaceutical compositions comprising as active ingredient at least one compound of formula (I), an isomer thereof, or an addition salt thereof with a pharmaceutically acceptable acid or base, alone or in combination with one or more pharmaceutically acceptable, inert, non-toxic excipients or carriers.

Among the pharmaceutical compositions according to the invention, there may be mentioned, more especially, those that are suitable for oral, parenteral (intravenous, intramuscular or subcutaneous), per- or trans-cutaneous, intravaginal, rectal, nasal, perlingual, buccal, ocular or respiratory administration.

Pharmaceutical compositions according to the invention for parenteral injections include, especially, aqueous and non-aqueous sterile solutions, dispersions, suspensions and emulsions, and also sterile powders for reconstituting injectable solutions or dispersions.

Pharmaceutical compositions according to the invention for oral administration in solid form include, especially, tablets or dragées, sublingual tablets, sachets, gelatin capsules and granules and, for oral, nasal, buccal or ocular administration in liquid form, include, especially, emulsions, solutions, suspensions, drop, syrups and aerosols.

Pharmaceutical compositions for rectal or vaginal administration are preferably suppositories, and those for per- or trans-cutaneous administration include, especially, powders, aerosols, creams, ointments, gels and patches.

The pharmaceutical compositions mentioned hereinbefore illustrate the invention but do not limit it in any way.

Among the pharmaceutically acceptable, inert, non-toxic excipients or carriers there may be mentioned, by way of non-limiting example, diluents, solvents, preservatives, wetting agents, emulsifiers, dispersing agents, binders, swelling agents, disintegrating agents, retardants, lubricants, absorbents, suspending agents, colorants, flavourings etc.

The useful dosage varies according to the age and weight of the patient, the administration route and the pharmaceutical composition used, the nature and severity of the disorder and the administration of any associated treatments. The dosage ranges from 1 mg to 500 mg per day in one or more administrations.

The Examples that follow illustrate the invention but do not limit it in any way.

The starting materials used are products that are known or that are prepared according to known operating procedures. The various Preparations yield synthesis intermediates that are useful in the preparation of the compounds of the invention.

The structures of the compounds described in the Examples and Preparations were determined according to the usual spectrophotometric techniques (infrared, nuclear magnetic resonance, mass spectrometry, . . . ).

The melting points were determined using either a Kofler hot-plate or a hot-plate under a microscope. When the compound is in the form of a salt, the melting point given and the elemental microanalysis refer to the salt form of the product.

Preparation 1:

Ethyl(1S,2S), (1R,2R)-1-[(tert-butoxycarbonyl)amino]-2-methylcyclopropanecarboxylate Step 1: Diethyl 2-methyl-1,1-cyclopropanedicarboxylate To a solution of 50.6 g of trimethylsulphoxonium iodide in 400 $cm^3$ of dimethyl sulphoxide there are added, in one go, 8.84 g of 60% sodium hydride in oil. The reaction mixture is stirred for 2 hours and then a solution of 43.3 g of diethyl ethylidenemalonate in 200 $cm^3$ of dimethyl sulphoxide is added dropwise over a period of 15 minutes. After stirring for 16 h, a mixture of ice and 100 $cm^3$ of 1N hydrochloric acid is added and then the reaction mixture is extracted with ether (3×200 $cm^3$). The combined organic phases are washed with sodium chloride solution and then dried over sodium sulphate and evaporated. Chromatography on silica gel (dichloromethane/cyclohexane: 75/25) allows 37.5 g of expected product to be isolated.

Step 2: (1R,2S), (1S,2R)-1-(Ethoxycarbonyl)-2-methylcyclopropanecarboxylic Acid

195 $cm^3$ of 1N sodium hydroxide solution are added dropwise to a solution of 37.5 g of the compound obtained in the above Step 1 in 400 $cm^3$ of ethanol. The reaction mixture is stirred for 16 hours at ambient temperature. After evaporation of the ethanol and dilution with 50 $cm^3$ of aqueous sodium chloride solution, the residual aqueous phase is washed with ether (2×50 $cm^3$) and then acidified with 48 $cm^3$ of 4N hydrochloric acid. The reaction mixture is again extracted with ether (2×100 $cm^3$), and the combined organic phases are dried over sodium sulphate and evaporated to obtain 29.4 g of the expected product.

Diastereoisomeric ratio: 95/5

Step 3: Ethyl(1S,2S), (1R,2R)-1-[(tert-butoxycarbonyl)amino]-2-methylcyclopropanecarboxylate Under an inert atmosphere and at ambient temperature, a solution of 22 $cm^3$ of diphenylphosphoryl azide in 30 $cm^3$ of toluene is added dropwise to a solution of 17.2 g of the compound obtained in the above Step 2, 13 $cm^3$ of triethylamine and 27 $cm^3$ of tert-butanol in 150 $cm^3$ of toluene. The reaction mixture is then heated for 16 hours at 85° C. with stirring. The cooled reaction mixture is washed with sodium carbonate solution and then with sodium chloride solution. After drying over sodium sulphate, evaporation and chromatography on silica gel (dichloromethane/cyclohexane: 75/25 then dichloromethane/tetrahydrofuran: 98/2), 14.03 g of the expected product are obtained.

Preparation 2:

tert-Butyl(1S,2S), (1R,2R)-1-(hydroxymethyl)-2-methylcyclopropylcarbamate

41 $cm^3$ of 2M lithium borohydride solution in tetrahydrofuran are added dropwise to a solution of 10 g of the product of Preparation 1 in 40 $cm^3$ of tetrahydrofuran. The solution is stirred for 20 hours at ambient temperature. After cooling in an ice bath and hydrolysing with 20 $cm^3$ of water, the reaction mixture is dried over sodium sulphate and then the tetrahydrofuran is evaporated off. Chromatography on silica gel of the residue obtained (dichloromethane then dichloromethane/methanol: 95/5), allows 7.2 g of the expected product to be obtained.

Preparation 3:

[(1R,2S), (1S,2R)-2-Methyl-1-(methylamino)cyclopropyl]methanol

Step 1: Ethyl(1R,2S), (1S,2R)-1-isocyano-2-methylcyclopropanecarboxylate

A solution of 2.5 g of ethyl isocyanate, 2.3 cm$^3$ of 1,2-dibromopropane, 25 cm$^3$ of dimethyl sulphoxide and 60 cm$^3$ of ether is added dropwise, over a period of one hour, to a suspension of 1.93 g of 60% sodium hydride in oil in 20 cm$^3$ of ether. After refluxing for 2 hours, the reaction mixture is cooled and poured into a mixture of 50 cm$^3$ of ice-water and 50 cm$^3$ of ether. The aqueous phase is separated off and extracted again with ether (3×40 cm$^3$). The combined organic phases are washed with aqueous sodium chloride solution, dried over sodium sulphate and evaporated. Chromatography on silica gel (dichloromethane/tetrahydrofuran: 97/3) allows 4.88 g of the expected product to be obtained.

Diastereoisomeric ratio: 90/10.

Step 2: [(1R,2S), (1R,S2R)-2-Methyl-1-(methylamino)cyclopropyl]methanol

A solution of 4.88 g of the compound obtained in the above Step 1 in 85 cm$^3$ of ether is added dropwise to a suspension of 3.73 g of lithium aluminium hydride in 250 cm$^3$ of ether. The reaction mixture is refluxed for 4 hours and then stirred for 16 hours at ambient temperature. The reaction mixture is cooled in an ice bath before the addition of sodium sulphate impregnated with water. After stirring for two hours, the minerals are filtered off and the ethereal phase is dried over sodium sulphate and then evaporated to obtain 2.75 g of the expected product.

Diastereoisomeric ratio: 90/10.

EXAMPLE 1

(1S,2S), (1R,2R)-N,2-dimethyl-1-[(3-pyridinyloxy)methyl]cyclopropanamine hydrochloride Step 1: Ethyl(1S,2S), (1R,2R)-1-[benzyl(tert-butoxycarbonyl)amino]-2-methylcyclopropanecarboxylate 21.5 g of potassium tert-butanolate are added at ambient temperature to a solution of 39 g of the compound of Preparation 1 in 400 cm$^3$ of dimethylformamide. The reaction mixture is stirred for one hour and then 35.9 g of benzyl bromide are added over a period of 30 minutes. After stirring for 16 hours, the dimethylformamide is evaporated off. The residue is taken up in 400 cm$^3$ of ether. The organic phase obtained is washed in succession with solutions of lithium chloride and of sodium carbonate and then dried over sodium sulphate and evaporated. Chromatography on silica gel (dichloromethane then dichloromethanelbutanone: 95/5) allows 41.4 g of the expected product to be obtained.

Step 2: Ethyl(1S,2S), (1R,2R)-1-[benzyl(methyl)amino]-2-methylcyclopropanecarboxylate A solution of 41.2 g of the compound obtained in the above Step 1 in 410 cm$^3$ of formic acid and 410 cm$^3$ of 37% aqueous formaldehyde solution is refluxed for two hours thirty minutes. The reaction mixture is then concentrated and taken up in a mixture of ether and aqueous sodium carbonate solution. After removing insoluble material by filtration, the aqueous phase is separated off and extracted with ether again. The combined ethereal phases are dried over sodium sulphate and then concentrated. The residue is taken up in 200 cm$^3$ of cyclohexane. After removing a small amount of insoluble material by filtration and evaporating the cyclohexane, 30 g of the expected product are obtained Step 3: {(1S,2S), (1R,2R)-1-[Benzyl(methyl)amino]-2-methylcyclopropyl}methanol A solution of 29.7 g of the compound obtained in the above Step 2 in 150 cm$^3$ of ether is added dropwise to a suspension of 4.55 g of lithium aluminium hydride in 300 cm$^3$ of ether. The reaction mixture is stirred for 20 hours and then cooled in an ice bath before the addition of sodium sulphate impregnated with water. After stirring for two hours, the minerals are filtered off and the ethereal phase is dried over sodium sulphate and then evaporated to yield 24 g of the expected product.

Step 4: (1S,2S), (1R,2R)-N-Benzyl-N,2-dimethyl-1-[(3-pyridinyloxy)methyl]cyclopropanamine In an 80 cm$^3$ reactor, 2.4 g of potassium tert-butanolate are added to a solution of 4 g of the compound obtained in the above Step 3 and 6 cm$^3$ of 3-fluoropyridine in 40 ml of dimethyl sulphoxide. The reaction mixture is heated for 8 minutes at 120° C. in a single-mode microwave oven. The whole operation is repeated twice. The three combined samples are poured into 600 cm$^3$ of aqueous sodium carbonate solution. The reaction mixture is extracted three times with ether. The combined ethereal phases are washed with sodium carbonate solution, dried over sodium sulphate and concentrated to yield 16.3 g of expected product.

Step 5: (1S,2S), (1R,2R)-N,2-Dimethyl-1-[(3-pyridinyloxy)methyl]cyclopropanamine Hydrochloride 28.4 cm$^3$ of 1N hydrochloric acid are added to a solution of 4 g of the compound obtained in the above Step 4 in 120 cm$^3$ of ethanol. The reaction mixture is hydrogenated for 2 hours under atmospheric pressure at ambient temperature in the presence of 1 g of palladium hydroxide (20% on carbon). The catalyst is filtered off and the solvents are evaporated. The residue is taken up in ethanol and concentrated again to yield 3.6 g of the expected product.

Mass spectrometry (ESI): m/z=193.1 Th [M+H]$^+$

Melting point (cap): 188-190° C. (recrystallisation from ethanol)

Step 6: Separation of the Enantiomers of the Compound of Example 1

3.5 g of compound of Example 1 are chromatographed on a Chiralpack AD column (ethanol, diethylamine) to obtain, after conversion to a salt using ethanolic hydrochloric acid solution and crystallisation, 2 g of the dihydrochloride of a first enantiomer α and 2.1 g of the dihydrochloride of the second enantiomer β.

EXAMPLE 2

α Enantiomer (1S,2S)- or (1R,2R)-(−)-N,2-dimethyl-1-[(3-pyridinyloxy)methyl]cyclopropanamine Dihydrochloride Mass spectrometry (EI): m/z=192 Th (M$^{+-}$)

Melting point (cap): 174-176° C.

Optical rotation: $[\alpha]_D^{19.7}$: −19.46° (c=0.01 g/cm$^3$, ethanol).

EXAMPLE 3

β Enantiomer (1S,2S)- or (1R,2R)-(+)-N,2-dimethyl-1-[(3-pyridinyloxy)methyl]cyclopropanamine dihydrochloride Mass spectrometry (CI) (NH$_3$): m/z=193 Th ([M+H]$^+$)

Melting point (cap): 174-176° C.

Optical rotation: $[\alpha]_D^{19.7}$: +17° (c=0.01 g/cm$^3$, ethanol)

EXAMPLE 4

(1S,2S), (1R,2R)-2-Methyl-1-[(3-pyridinyloxy)methyl]cyclopropanamine

Step 1: [(1S,2S), (1R,2R)-1-Amino-2-methylcyclopropyl]methanol Hydrochloride 20 cm$^3$ of 4N hydrochloric acid solution in dioxane are added to a solution of 7 g of the compound of Preparation 2 in 20 cm$^3$ of ethanol. After stirring for 20 hours, the solvents are evaporated off. 20 cm$^3$ of dioxane and 150 cm$^3$ of ether are added to the residue and, after stirring for 20 hours, the expected hydrochloride is filtered off and dried. 4.6 g of the expected product are obtained.

Step 2: (1S,2S), (1R,2R)-2-Methyl-1-[(3-pyridinyloxy)methyl]cyclopropanamine 12.5 g of potassium tert-butanolate are added to a solution of 4.5 g of the product obtained in the above Step 1 in 75 cm$^3$ of dimethyl sulphoxide. After stirring for 30 minutes, 22 cm$^3$ of 3-fluoropyridine are added and stirring is continued for 6 hours. The reaction mixture is poured into aqueous sodium carbonate solution and extracted with ethyl acetate. The organic phase is washed with aqueous sodium carbonate solution and then dried over sodium sulphate and concentrated. Chromatography on silica gel of the residue obtained (dichloromethane/methanol: 95/5) allows 3.2 g of expected product to be obtained.

Step 3: Separation of the Enantiomers of the Compound of Example 4

3.15 g of the compound of Example 4 are chromatographed on a Chiralpack AD column (methanol, diethylamine) to obtain, after conversion to a salt using 4N hydrochloric acid solution in dioxane and crystallisation, 1.75 g of the dihydrochloride of a first enantiomer α and 1.7 g of the dihydrochloride of the second enantiomer β.

EXAMPLE 5

α Enantiomer (1S,2S)- or (1R,2R)-(−)-2-methyl-1-[(3-pyridinyloxy)methyl]cyclopropanamine dihydrochloride Mass spectrometry (ESI): m/z=179.1 Th ([M+H]$^+$)

Melting point: <75° C. (gum)

Optical rotation: [α]$_D^{20}$: −23.14° (c=0.01054 g/cm$^3$, ethanol).

EXAMPLE 6

β Enantiomer (1S,2S)- or (1R,2R)-(+)-2-methyl-1-[(3-pyridinyloxy)methyl]cyclopropanamine dihydrochloride Mass spectrometry (ESI): m/z=179.1 Th ([M+H]$^+$)

Melting point: <75° C. (gum)

Optical rotation: [α]$_D^{20}$: =+22.14° (c=0.01055 g/cm$^3$, ethanol)

EXAMPLE 7

(1S,2S), (1R,2R)-N,N,2-Trimethyl-1-[(3-pyridinyloxy)methyl]cyclopropanamine

Step 1: (1S,2S), (1R,2R)-N,N,2-Trimethyl-1-[(3-pyridinyloxy)methyl]cyclopropanamine A solution of 3.6 g of the compound of Example 4 in 40 cm$^3$ of formic acid and 40 cm$^3$ of 37% aqueous formaldehyde solution is refluxed for 4 hours. The reaction mixture is poured into aqueous sodium carbonate solution and extracted with ethyl acetate. The organic phase is dried over sodium sulphate and then concentrated. Chromatography on silica gel of the residue obtained (dichloromethane/methanol: 97/3) allows 2.6 g of the expected compound to be obtained.

Step 2: Separation of Thte Enantiomers of the Compound of Example 7

3.9 g of the compound of Example 7 are chromatographed on a Chiralpack AD column (methanol, acetonitrile, diethylamine) to obtain, after conversion to a salt using 4N hydrochloric acid in dioxane, 2.3 g of the dihydrochloride of the first enantiomer α and 2.3 g of the dihydrochloride of the second enantiomer β.

EXAMPLE 8

α Enantiomer (1S,2S), (1R,2R)-(+)-N,N,2-Trimethyl-1-[(3-pyridinyloxy)methyl]cyclopropanamine dihydrochloride Mass spectrometry (ESI): m/z=201.7 Th ([M+H]$^+$)

Melting point (cap): 171-173° C.

Optical rotation: [α]$_D^{20}$: =+15.790° (c=0.01014 g/cm$^3$, ethanol)

EXAMPLE 9

β Enantiomer (1S,2S), (1R,2R)-(−)-N,N,2-Trimethyl-1-[(3-pyridinyloxy)methyl]cyclopropanamine dihydrochloride Mass spectrometry (ESI): m/z=207.1 Th ([M+H]$^+$)

Melting point (cap): 172-173° C.

Optical rotation: [α]$_D^{20}$: =−16.64° (c=0.01016 g/cm$^3$, ethanol)

EXAMPLE 10

(1S,2S), (1R,2R)-1-{[(6-Chloro-3-pyridinyl)oxy]methyl}-N,2-dimethylcyclopropanamine Step 1: Ethyl(1S,2S), (1R,2R)-1-[(tert-butoxycarbonyl)(methyl)amino]-2-methylcyclopropanecarboxylate 5.5 g of potassium tert-butanolate are added at ambient temperature to a solution of 11.3 g of the compound of Preparation 1 in 175 cm$^3$ of dimethylformamide. The reaction mixture is stirred for 45 minutes and then 3.2 cm$^3$ of methyl iodide are added dropwise. After stirring for 16 hours, 200 cm$^3$ of aqueous sodium carbonate solution are added and the reaction mixture is extracted three times with ether. The combined organic phases are washed with lithium chloride solution and then dried over sodium sulphate and evaporated. Chromatography on silica gel (dichloromethane/cyclohexane: 75/25) allows 9.17 g of the expected product to be obtained.

Step 2: tert-Butyl(1S,2S), (1R,2R)-1-(hydroxymethyl)-2-methylcyclopropyl(methyl)-carbamate 65 cm$^3$ of 2M lithium borohydride solution in tetrahydrofuran are added dropwise to a solution of 10 g of the compound obtained in the above Step 1 in 45 cm$^3$ of tetrahydrofuran. The solution is stirred for three days at 60° C. After cooling in an ice bath and hydrolysing with 100 cm$^3$ of water, the reaction mixture is extracted three times with ether. The combined organic phases are dried over sodium sulphate and evaporated. Chromatography on silica gel (dichloromethane/tetrahydrofuran: 97/3) allows 5.26 g of the expected product to be obtained.

Step 3: tert-Butyl(1S,2S), (1R,2R)-1-(bromomethyl)-2-methylcyclopropyl(methyl)-carbamate 2.42 g of triphenylphosphine and then 3.05 g of tetrabromomethane are added in succession to a solution of 2 g of the compound obtained in the above Step 2 in 48 cm³ of ether. After stirring for 20 hours, the reaction mixture is filtered and the filtrate is concentrated. Chromatography on silica gel (dichloromethane/cyclohexane: 75/25) allows 1.85 g of the expected product to be obtained.

Step 4: tert-Butyl(1S,2S), (1R,2R)-1-{[(6-chloro-3-pyridinyl)oxy]methyl}-2-methylcyclopropyl(methyl)carbamate 12.4 g of caesium carbonate are added to a solution of 5.3 g of the compound obtained in the above Step 3 and 4.9 g of 6-chloropyridin-3-ol in 100 cm³ of butanone. After refluxing for 20 hours, the minerals are filtered off and the butanone is evaporated. The residue is taken up in ethyl acetate and the organic phase obtained is washed with aqueous sodium carbonate solution and then dried over sodium sulphate and concentrated. Chromatography on silica gel (dichloromethane/butanone: 95/5) allows 4 g of the expected product to be obtained.

Step 5: (1S,2S), (1R,2R)-1-{[(6-Chloro-3-pyridinyl)oxy]methyl}-N,2-dimethylcyclopropanamine 15 cm³ of 4N hydrochloric acid solution in dioxane are added to a solution of 4 g of the compound obtained in the above Step 4 in 15 cm³ of dioxane. After stirring for 20 hours, the reaction mixture is diluted with ether and then 3.5 g of the hydrochloride of the expected product are filtered off. The hydrochloride is taken up in aqueous sodium carbonate solution. After extracting with dichloromethane, drying the organic phase over sodium sulphate and evaporating off the solvent, 2.5 g of the expected product are obtained.

Step 6: Separation of the Enantiomers of the Compound of Example 10

4.5 g of the compound of Example 10 are chromatographed on a Chiralpack AD column (methanol/diethylamine: 1000/1) to obtain, after conversion to a salt using 4N hydrochloric acid in dioxane and crystallisation, 2.35 g of the dihydrochloride of the first enantiomer α and 2.2 g of the dihydrochloride of the second enantiomer β.

EXAMPLE 11

α Enantiomer (1S,2S)- or (1R,2R)-(−)-1-{[(6-chloro-3-pyridinyl)oxy]methyl}-N,2-dimethylcyclopropanamine Hydrochloride Mass spectrometry (ESI): m/z=227.1 Th ([M+H]$^+$)
Melting point (cap): 185-190° C.
Optical rotation: $[\alpha]_D^{20}$: =−13.90° (c=0.01079 g/cm³, methanol)

EXAMPLE 12

β Enantiomer (1S,2S)- or (1R,2R)-(+)-1-{[(6-chloro-3-pyridinyl)oxy]methyl}-N,2-dimethylcyclopropanamine Hydrochloride Mass spectrometry (ESI): m/z=227.1 Th ([M+H]$^+$)
Melting point (cap): 188-192° C.
Optical rotation: $[\alpha]_D^{20}$: =+15.13° (c=0.01062 g/cm³, methanol)

EXAMPLE 13

(1S,2S), (1R,2R)-1-{[(6-Chloro-3-pyridinyl)oxy]methyl}-2-methylcyclopropanamine

Step 1: tert-Butyl(1S,2S), (1R,2R)-1-(bromomethyl)-2-methylcyclopropylcarbamate

The compound is obtained in accordance with the procedure of Step 3 of Example 10, with replacement of the compound of Step 2 of Example 10 with the compound of Preparation 2.

Step 2: tert-Butyl(1S,2S), (1R,2R)-1-{[(6-chloro-3-pyridinyl)oxy]methyl}-2-methylcyclopropylcarbamate The compound is obtained in accordance with the procedure of Step 4 of Example 10, with replacement of the compound of Step 3 of Example 10 with the compound of the above Step 1.

Step 3: (1S,2S), (1R,2R)-1-{[(6-Chloro-3-pyridinyl)oxy]methyl}-2-methylcyclopropanamine The compound is obtained in accordance with the procedure of Step 5 of Example 10, with replacement of the compound of Step 4 of Example 10 with the compound of the above Step 2.

Step 4: Separation of the Enantiomers of the Compound of Example 13

2 g of the compound of Example 13 are chromatographed on a Chiralpack AD column (isopropanol/diethylamine) to obtain, after conversion to a salt using 4N hydrochloric acid solution in dioxane and crystallisation, 1.05 g of the hydrochloride of the first enantiomer ax and 1.1 g of the hydrochloride of the second enantiomer β.

EXAMPLE 14

α Enantiomer (1S,2S)- or (1R,2R)-(−)-1-{[(6-chloro-3-pyridinyl)oxy]methyl}-2-methylcyclopropanamine Hydrochloride Mass spectrometry (ESI): m/z=213.1 Th ([M+H]$^+$)
Melting point (cap): 183-186° C.
Optical rotation: $[\alpha]_D^{20}$: =−15.89° (c=0.0101 g/cm³, methanol)

EXAMPLE 15

β Enantiomer (1S,2S)- or (1R,2R)-(+)-1-{[(6-chloro-3-pyridinyl)oxy]methyl}-2-methylcyclopropanamine Hydrochloride Mass spectrometry (ESI): m/z=213.1 Th ([M+H]$^+$)
Melting point (cap): 183-186° C.
Optical rotation: $[\alpha]_D^{20}$: =+16.49° (c=0.01015 g/cm³, methanol)

EXAMPLE 16

(1S,2S), (1R,2R)-1-{[(6-Chloro-3-pyridinyl)oxy]methyl}-N,N,2-trimethylcyclopropanamine Step 1: (1S,2S), (1R,2R)-1-[[(6-Chloro-3-pyridinyl)oxy]methyl]-N,N,2-trimethylcyclopropanamine The compound is obtained in accordance with the procedure of Step 1 of Example 7, with replacement of the compound of Example 4 with the compound of Example 10.

Step 2: Separation of the Enantiomers of the Compound of Example 16

2.4 g of the compound of Example 16 are chromatographed on a Chiralpack AD column (isopropanol/diethylamine: 100/1) to obtain, after conversion to a salt using 4N hydrochloric acid solution in dioxane and crystallisation, 1.1 g of the hydrochloride of the first enantiomer α and 1.05 g of the hydrochloride of the second enantiomer β.

EXAMPLE 17

α Enantiomer (1S,2S)- or (1R,2R)-(+)-1-{([(6-chloro-3-pyridinyl)oxy]methyl}-N,N,2-trimethylcyclopropanamine Hydrochloride
  Mass spectrometry (ESI): m/z=241.1 Th ([M+H]$^+$)
  Melting point (cap): 136-138° C.
  Optical rotation: $[\alpha]_D^{20}$: =+12.640° (c=0.01055 g/cm$^3$, methanol)

EXAMPLE 18

α Enantiomer (1S,2S)- or (1R,2R)-(−)-1-{[(6-chloro-3-pyridinyl)oxy]methyl}-N,N,2-trimethylcyclopropanamine Hydrochloride
  Mass spectrometry (ESI): m/z=241.1 Th ([M+H]$^+$)
  Melting point (cap): 136-138° C.
  Optical rotation: $[\alpha]_D^{20}$: =−11.23° (c=0.01055 g/cm$^3$, methanol)

EXAMPLE 19

(1S,2R), (1R,2S)-N,2-Dimethyl-1-[(3-pyridinyloxy)methyl]cyclopropanamine Dihydrochloride Step 1: (1S,2R), (1R,2S)-N,2-Dimethyl-1-[(3-pyridinyloxy)methyl]cyclopropanamine Dihydrochloride 2.6 g of potassium tert-butanolate and 9.2 cm$^3$ of 3-fluoropyridine are added to a solution of 2.25 g of the compound of Preparation 3 in 75 cm$^3$ of dimethyl sulphoxide. The reaction mixture is heated for 90 seconds at 30% of the maximum power of a 1000 W multimode microwave oven. After cooling, the reaction mixture is poured into aqueous sodium chloride solution and extracted several times with ethyl acetate. The combined organic phases are washed with sodium chloride solution and then dried over sodium sulphate and evaporated. Chromatography on silica gel (dichloromethane/methanol/ammonium hydroxide) allows 2.46 g of the non-salt-form product to be obtained in the form of a single diastereoisomer. After conversion of the compound to a salt using 4N hydrochloric acid in dioxane and crystallisation, 1.22 g of the expected compound are obtained.
  Mass spectrometry (ESI): m/z=193.1 Th ([M+H]$^+$)
  Melting point (cap): 189-191° C.

Step 2: Separation of the Enantiomers of the Compound of Example 19

1.8 g of the compound of Example 19 are chromatographed on a Chiralpack AD column (ethanol/acetonitrile/diethylamine: 150/850/1) to obtain, after conversion to a salt using 4N hydrochloric acid solution in dioxane and crystallisation, 0.54 g of the hydrochloride of the first enantiomer α and 0.58 g of the hydrochloride of the second enantiomer β.

EXAMPLE 20

α Enantiomer (1S,2R)- or (1R,2S)-(+)-N,2-dimethyl-1-[(3-pyridinyloxy)methyl]cyclopropanamine Dihydrochloride
  Mass spectrometry (ESI): m/z=193.1 Th ([M+H]$^+$)
  Melting point (cap): 69-72° C.
  Optical rotation: $[\alpha]_D^{20}$: =+30.04° (c=0.01084 g/cm$^3$, ethanol)

EXAMPLE 21

α Enantiomer (1S,2R)- or (1R,2S)-(−)-N,2-dimethyl-1-[(3-pyridinyloxy)methyl]cyclopropanamine Dihydrochloride
  Mass spectrometry (ESI): m/z=193.1 Th ([M+H]$^+$)
  Melting point (cap): 71-74° C.
  Optical rotation: $[\alpha]_D^{20}$: =−31.24° (c=0.00961 g/cm$^3$, ethanol)

EXAMPLE 22

(1S,2R), (1R,2S)-1-{[(5-Bromo-3-pyridinyl)oxy]methyl}-N,2-dimethylcyclopropanamine Dihydrochloride 1.7 g of 60% sodium hydride in oil are added to 4.6 g of the compound of Preparation 3 in 160 cm$^3$ of dimethylformamide. The reaction mixture is stirred for one hour at ambient temperature and then 10.2 g of 3,5-dibromopyridine are added dropwise. The reaction mixture is heated for 16 hours at 60° C. and then the dimethylformamide is evaporated off. The residue is taken up in 300 cm$^3$ of ether. The organic phase is washed with aqueous lithium chloride solution and then dried over sodium sulphate and concentrated. Chromatography on silica gel (dichloromethane/methanol: 96/4) allows 4.86 g of the non-salt-form compound to be obtained. After conversion to a salt of 0.43 g of the compound in ethanol using 1 cm$^3$ of 4N hydrochloric acid solution in dioxane, the solvents are evaporated off and the residue is recrystallised from ethanol to obtain 0.35 g of the expected product.
  Mass spectrometry (ESI): m/z=271.1 Th ([M+H]$^+$)
  Melting point (cap): 157-159° C.

EXAMPLE 23

(1S,2R), (1R,2S)-2-Methyl-1-[(3-pyridinyloxy)methyl]cyclopropanamine Dihydrochloride Step 1: Ethyl(2E)-2-cyano-2-butenoate 2 cm$^3$ of piperidine are added dropwise to a solution of 64 cm$^3$ of ethyl cyanoacetate and 34 cm$^3$ of acetaldehyde in 80 cm$^3$ of acetic acid. After stirring for 20 hours at ambient temperature, the reaction mixture is diluted with 200 cm$^3$ of water and extracted with ether (3×200 cm$^3$). The combined organic phases are washed with water and then dried over sodium sulphate and evaporated. Distillation under reduced pressure (97° C./10 torr) of the residue obtained allows 40.44 g of the expected product to be obtained.
  Diastereoisomeric ratio E/Z: 96/4.

Step 2: Ethyl(1S,2S), (1R,2R)-1-cyano-2-methylcyclopropanecarboxylate 1.92 g of 60% sodium hydride in oil are added in a single go to a solution of 17.6 g of trimethylsulphoxonium iodide in 120 cm³ of dimethyl sulphoxide. The reaction mixture is stirred for 2 hours and then a solution of 10 g of the compound obtained in the above Step 1 in 60 cm³ of dimethyl sulphoxide is added dropwise. After stirring for 16 hours, the reaction mixture is poured into a mixture of ice and 1N hydrochloric acid and is then extracted with ether (3×200 cm³). The combined organic phases are washed with aqueous sodium chloride solution and then dried over sodium sulphate and evaporated. Chromatography on silica gel (dichloromethane/tetrahydrofuran: 97/3) allows 7.15 g of the expected product to be isolated.

Step 3: (1S,2S), (1R,2R)-1-(Hydroxymethyl)-2-methylcyclopropanecarbonitrile

A solution of 2 g of the compound obtained in the above Step 2 in 20 cm³ of tetrahydrofuran is added dropwise to a solution of 4.92 g of sodium borohydride in 80 cm³ of tetrahydrofuran and 5 cm³ of water. The solution is then stirred for 7 hours at 50° C. and subsequently overnight at ambient temperature. 100 cm³ of methanol are cautiously added and then the reaction mixture is concentrated. The procedure is repeated once more and then the residue is, taken up in 100 cm³ of sodium hydrogen carbonate and extracted with dichloromethane. After a second extraction with dichloromethane, the combined organic phases are dried over sodium sulphate and evaporated. Chromatography on silica gel (dichloromethane/tetrahydrofuran: 97/3) allows 1.71 g of the expected product to be obtained.

Step 4: (1S,2S), (1R,2R)-2-Methyl-1-[(3-Pyridinyloxy)methyl]cyclopropanecarbonitrile 2.4 g of potassium tert-butanolate are added to a solution of 0.56 g of the product of the above Step 3 in 15 cm³ of dimethyl sulphoxide. After homogenisation, 2.2 cm³ of 3-fluoropyridine are added and the reaction mixture is heated for 5 minutes at 80° C. After cooling, the reaction mixture is diluted with 40 cm³ of aqueous sodium chloride solution and extracted several times with ethyl acetate. The combined organic phases are washed with sodium chloride solution and then dried over sodium sulphate and evaporated. Chromatography on silica gel (dichloromethane/tetrahydrofuran: 97/3) allows 0.71 g of the expected product to be obtained Step 5: (1R,2S), (1S,2R)-2-Methyl-1-[(3-pyridinyloxy)methyl]cyclopropanecarboxamide A mixture of 1 g of the product obtained in the above Step 4, 3.8 cm³ of 50% aqueous hydrogen peroxide solution and 0.32 g of lithium hydroxide in 10 cm³ of ethanol is stirred for 45 minutes at ambient temperature and then for 75 minutes at 45° C. The reaction mixture is filtered and insoluble material is washed with dichloromethane. The filtrate is concentrated and chromatography on silica gel (dichloromethane/methanol/ammonium hydroxide: 95/4/1) allows 0.94 g of the expected product to be obtained.

Step 6: (1S,2R), (1R,2S)-2-Methyl-1-[(3-pyridinyloxy)methyl]cyclopropanamine Dihydrochloride 0.25 cm³ of bromine are added to a solution of 1.64 g of potassium hydroxide in 10 cm³ of water. The solution is cooled to 0° C. and 1 g of the product prepared in the above Step 5 is added in one go. The reaction mixture is stirred vigorously for 15 minutes at ambient temperature and then for 45 minutes at 75° C. After cooling, the reaction mixture is diluted with 30 cm³ of aqueous sodium chloride solution and extracted several times with ethyl acetate. The combined organic phases are dried over sodium sulphate and evaporated. Chromatography on silica gel (dichloromethane/methanol/ammonium hydroxide: 95/4/1) allows 0.59 g of the non-salt-form product to be obtained. After conversion of 1.18 g of the compound to a salt using 4N hydrochloric acid solution in dioxane and recrystallisation from ethanol, 1.41 g of the expected product are obtained.

Mass spectrometry (ESI): m/z=179 Th ([M+H]⁺)
Melting point (cap): 188-190° C.

EXAMPLE 24

(1S,2R), (1R,2S)-N,N,2-Trimethyl-1-[(3-pyridinyloxy)methyl]cyclopropanamine Dihydrochloride The compound is obtained in accordance with the procedure of Step 1 of Example 7, with replacement of the compound of Example 4 with the compound of Example 23. After conversion to a salt of 0.88 g of the compound using 4N hydrochloric acid solution in dioxane, the solvents are evaporated off and the residue is recrystallised from ethanol to obtain 0.98 g of the expected product.

Mass spectrometry (ESI): m/z=207.1 Th ([M+H]⁺)
Melting point (cap): 196-200° C.

EXAMPLE 25

(R,S)-N,2,2-Trimethyl-1-[(3-pyridinyloxy)methyl]cyclopropanamine Dihydrochloride Step 1: Diethyl 2-(2-methylpropylidene)malonate A mixture of 69.80 g of 2-methylpropanal, 77.30 g of diethyl malonate, 2.06 g of benzoic acid, 2.47 cm³ of piperidine and 100 cm³ of toluene is stirred at reflux for 15 hours. After cooling, 100 cm³ of toluene are added. The solution is washed in succession twice with 100 cm³ of distilled water, twice with 100 cm³ of 1M hydrochloric acid and 100 cm³ of saturated aqueous sodium carbonate solution. The organic phase is dried over anhydrous sodium sulphate and concentrated. The residue obtained is distilled under reduced pressure (117° C./10 torr) to obtain 93.44 g of the expected product in the form of a colourless oil.

Step 2: Diethyl 2-(2-bromo-2-methylpropylidene)malonate 56.04 g of N-bromosuccinimide are added to a solution of 64.20 g of the compound obtained in the above Step 1 in 300 cm³ of carbon tetrachloride. The reaction mixture is stirred at reflux for 2 hours. After cooling to ambient temperature, the mixture is filtered and concentrated to obtain 89.8 g of expected product.

Step 3: Diethyl 2,2-dimethyl-1,1-cyclopropanedicarboxylate

A solution of 87.70 g of the compound obtained in the above Step 2 in 90 cm³ of ethanol is added dropwise to 24.3 g of sodium borohydride in 300 cm³ of ethanol. The reaction mixture is stirred for three hours at ambient temperature, then heated at 40° C. for 1 h 30. The solvent is evaporated off, and the residue is taken up in 200 cm³ of distilled water and extracted with dichloromethane (3×200 cm³). The combined organic phases are dried over sodium sulphate and concentrated to obtain 63.0 g of expected product.

Step 4: 1-(Ethoxycarbonyl)-2,2-dimethylcyclopropanecarboxylic Acid 270 cm³ of 1N sodium hydroxide are added at ambient temperature, over a period of 30 minutes, to a solution of 59.2 g of the compound obtained in the above Step 3 in 600 cm³ of ethanol. The reaction mixture is stirred 20 hours at ambient temperature and then the ethanol is evaporated off. The residual aqueous phase is extracted twice with ether, and then acidified with 25 cm³ of 37% hydrochloric acid, saturated with sodium chloride and extracted with ether again 6 times. The combined ethereal phases are dried over sodium sulphate and concentrated to obtain 41.2 g of expected product.

Step 5: Ethyl 1-[(tert-butoxycarbonyl)amino]-2,2-dimethyl-cyclopropanecarboxylate Under an inert atmosphere and at ambient temperature, a solution of 29.20 g of diphenylphosphoryl azide in 30 cm$^3$ of toluene is added dropwise to a solution of 19.77 g of the compound obtained in the above Step 4, 15.2 cm$^3$ of triethylamine and 23.6 g of tert-butanol in 150 cm$^3$ of toluene. The reaction mixture is then heated for 20 hours at 85° C. with stirring. After cooling, the reaction mixture is washed with 70 cm$^3$ of aqueous sodium carbonate solution. The aqueous phase is extracted 3 times with 100 cm$^3$ of toluene. The combined organic phases are dried over sodium sulphate and concentrated. Chromatography on silica gel (dichloromethane/tetrahydrofuran: 98/2) allows 12.75 g of expected product to be obtained.

Step 6: Ethyl 1-[(tert-butoxycarbonyl)(methyl)amino]-2,2-dimethylcyclopropanecarboxylate 16.6 g of potassium tert-butanolate are added with stirring, over a period of one hour, to a solution of 24.1 g of compound obtained in the above Step 5 in 240 cm$^3$ of dimethylformamide. The reaction mixture is stirred for 30 minutes at ambient temperature and then 20.0 g of methyl iodide are added dropwise. The mixture is stirred at ambient temperature for 2 hours. The reaction mixture is concentrated to dryness and the residue is taken up in 300 cm$^3$ of ether. The organic phase is washed with 40 cm$^3$ of aqueous sodium hydrogen carbonate solution and with aqueous lithium chloride solution (2×20 cm$^3$) and then dried over sodium sulphate and concentrated. Chromatography on silica gel (dichloromethane), allows 17.6 g of expected product to be obtained.

Step 7: Ethyl 2,2-dimethyl-1-(methylamino)cyclopropanecarboxylate 270 cm$^3$ of 8.7N hydrochloric acid solution in ethanol are added dropwise to a solution, cooled to 5° C., of 18.06 g of the compound obtained in the above Step 6 in 60 cm$^3$ of ethanol. The reaction mixture is stirred for 3 hours at ambient temperature and then concentrated to dryness. The residue is taken up in ethanol and then concentrated to dryness again 3 times in succession. Aqueous sodium hydrogen carbonate solution is added to the hydrochloride obtained, and the aqueous phase is extracted 5 times with dichloromethane. The combined organic phases are dried over sodium sulphate and then concentrated. 10.94 g of expected product are isolated.

Step 8: Ethyl 1-[benzoyl(methyl)amino]-2,2-dimethylcyclopropanecarboxylate

A solution of 9.88 g of benzoyl chloride in 40 cm$^3$ of tetrahydrofuran is added dropwise to a solution, cooled to 5° C., of 10.94 g of the compound obtained in the above Step 7 and 7.76 g of triethylamine in 170 cm$^3$ of tetrahydrofuran. The reaction mixture is stirred for 45 minutes at 5° C. and then for 2 hours at ambient temperature. The white precipitate formed is filtered off and washed with THF. The filtrate is concentrated to dryness. The residue obtained is diluted with dichloromethane and washed with saturated aqueous sodium carbonate solution. After separation, the aqueous phase is extracted 4 times with dichloromethane. The combined organic phases are then dried over sodium sulphate and concentrated to dryness. Chromatography on silica gel (dichloromethane/tetrahydrofuran: 95/5) allows 16.07 g of expected product to be obtained.

Step 9: {1-[Benzyl(methyl)amino]-2,2-dimethylcyclopropyl}methanol

A solution of 16.07 g of the compound obtained in the above Step 8 in 130 cm$^3$ of tetrahydrofuran is added dropwise to a suspension of 4.44 g of lithium aluminium hydride in 350 cm$^3$ of tetrahydrofuran. The mixture is refluxed for 4 hours. It is then cooled to 5° C. and subsequently hydrolysed with 4.5 cm$^3$ of distilled water, 4.5 cm$^3$ of 4N sodium hydroxide and 15 cm$^3$ of distilled water. After stirring for 30 minutes at ambient temperature, a precipitate is filtered off and rinsed with tetrahydrofuran. The filtrate is dried over sodium sulphate and concentrated to dryness. Chromatography on silica gel (dichloromethane (100) to dichloromethane/tetrahydrofuran: 95/5), allows 11.9 g of expected product to be isolated.

Step 10: N-Benzyl-N,2,2-trimethyl-1-[(3-pyridinyloxy)methyl]cyclopropanamine 1.86 g of potassium tert-butanolate are added to a solution of 3.2 g of the product obtained in the above Step 9 in 96 cm$^3$ of dimethyl sulphoxide. After stirring for a few seconds, 6.3 cm$^3$ of 3-fluoropyridine are added. The reaction mixture is refluxed for 2 minutes in a 1000 W multimode microwave oven. After cooling, the reaction mixture is poured into 300 cm$^3$ of saturated aqueous sodium chloride solution and then extracted 6 times with ether. The combined organic phases are washed with sodium chloride solution and then dried over sodium sulphate and evaporated. Chromatography on silica gel (dichloromethane) of the residue obtained allows 3.83 g of expected product to be obtained.

Step 11: (R,S)-N,2,2-Trimethyl-1-[(3-pyridinyloxy)methyl]cyclopropanamine Dihydrochloride 8.8 cm$^3$ of 1N hydrochloric acid are added to a solution of 1.35 g of the compound obtained in the above Step 10 in 40 cm$^3$ of ethanol. The reaction mixture is hydrogenated for 5 hours under atmospheric pressure, at ambient temperature, in the presence of 0.27 g of palladium hydroxide (20% on carbon). The catalyst is filtered off and the solvents are evaporated off. The residue is taken up in 30 cm$^3$ of saturated aqueous sodium carbonate solution and then extracted with ether. The ethereal phases are dried over sodium sulphate and then concentrated to dryness. 20 cm$^3$ of 4N hydrochloric acid solution in ether are added to the residue and the hydrochloride formed is filtered off. After drying, 0.79 g of the expected compound is obtained.

Mass spectrometry (ESI): m/z=207.1 Th ([M+H]$^+$)

Melting point (cap): 86-88° C.

Step 12: Separation of the Enantiomers of the Compound of Example 25

The separation of the enantiomers of 2.80 g of the racemic product obtained in Step 10 of Example 25 was carried out by chiral chromatography on a Chiracel OJ column (ethanol). 1.43 g of the first enantiomer α and 1.37 g of the second enantiomer β are isolated in that way.

α Enantiomer (R or S)-(+)-N-Benzyl-N,2,2-trimethyl-1-[(3-pyridinyloxy)methyl]cyclopropanamine or (R or S)-(−)-N-Benzyl-N,2,2-trimethyl-1-[(3-pyridinyloxy)methyl]cyclopropanamine β Enantiomer (R or S)-(+)-N-Benzyl-N,2,2-trimethyl-1-[(3-pyridinyloxy)methyl]cyclopropanamine or (R or S)-(−)-N-Benzyl-N,2,2-trimethyl-1-[(3-pyridinyloxy)-methyl]cyclopropanamine enantiomeric ratio (α enantiomer): 97.2/2.8 enantiomeric ratio (β enantiomer): 99.1/0.9

EXAMPLE 26

α Enantiomer (R or S)-(+)-N,2,2-trimethyl-1-[(3-pyridinyloxy)methyl]cyclopropanamine difumarate Debenzylation of the α enantiomer obtained in Step 12 of Example 25 was carried out in accordance with the procedure described in Step 11 of Example 25. The fumarate of 1.4 g of the α enantiomer is obtained by dissolution of the base in ethanol in the presence of 1.5 equivalents of fumaric acid. The solution is concentrated to dryness and then taken up in ether. 0.83 g of the fumarate is obtained by filtration and drying.

Mass spectrometry (ESI): m/z=207.1 Th ([M+H]$^+$)

Melting point (cap): 124-127° C.

Optical rotation: $[\alpha]_D^{20}$: +13.5° (c=0.01249 g/cm$^3$, CH$_3$OH).

EXAMPLE 27

β Enantiomer (R or S)-(−)-N,2,2-trimethyl-1-[(3-pyridinyloxy)methyl]cyclopropanamine Difumarate The compound is obtained according to the procedure of Example 27, with replacement of the α enantiomer with the β enantiomer.

Mass spectrometry (ESI): m/z=207.1 Th ([M+H]$^+$)

Melting point (cap): 115-118° C.

Optical rotation: $[\alpha]_D^{20}$: −14.1° (c=0.0099 g/cm$^3$, CH$_3$OH)

PHARMACOLOGICAL STUDIES OF COMPOUNDS OF THE INVENTION

EXAMPLE A

Displacement of Binding of [$^{125}$I]-α-Bungarotoxin on Nicotinic Receptors of the Electric Organ of Torpedo Fish This study, carried out according to the method described in J. Pharmacol. Exp. Ther., 1994, 271 624-631, is aimed at assessing the affinity of compounds of the present invention for nicotinic receptors of the "muscular" type.

Membranes (1-5 μg/ml) of the electric organ of torpedo fish are incubated (1 hour, 22° C.) in the presence of a series of concentrations (0.01-10 μM) of each compound of the invention (diluted starting from a 10 mM stock solution in DMSO) in the presence of [$^{125}$I]-α-bungarotoxin (S.A.: 7.4 TBq/mmol: 0.2 nM) in Krebs buffer (Tris-HCl 50 mM, KCl 5 mM, MgCl$_2$ 1 mM, CaCl$_2$ 2 mM, NaCl 100 mM, pH 7.4) with 0.01% BSA; final volume: 500 μl. The non-specific binding is determined by incubating membranes in the presence of α-bungarotoxin (1 μM).

The results show that, up to a concentration of 10 μM, all of the compounds of the present invention have no significant affinity for nicotinic receptors of the "muscular" type ($K_i$>10$^{-5}$M).

EXAMPLE B

Displacement of Binding of [$^3$H]-epibatidine on Nicotinic Receptors of IMR32 Cells This study, carried out according to the technique described in Molec. Pharmacol., 1995, 48; 280-287, is aimed at determining the affinity of compounds of the present invention for nicotinic receptors of the "ganglionic" type (American Soc. Neuroscience, 2000, 26, 138).

Membranes (250 μg/ml) of IMR-32 neuroblastoma cells are incubated (2 hours, 20° C.) in the presence of a series of concentrations (0.01-10 μM) of each compound of the invention (diluted starting from a 10 mM stock solution in DMSO) and (±)-[$^3$H]-epibatidine (S.A.: 2464 GBq/mmol: 1.5 nM) in phosphate buffer (NaH$_2$PO$_4$ 20 mM, pH 7.4); final volume: 250 μl. The non-specific binding is determined by incubating membranes in the presence of 300 μM of (−)nicotine.

The results show that, up to a concentration of 10 μM, all of the compounds of the present invention have no significant affinity for nicotinic receptors of the "ganglionic" type ($K_i$>10$^{-5}$M).

EXAMPLE C

Displacement of Binding of [$^3$H]-oxotremorine-M on Muscarinic Receptors of Rat Brain This study, carried out according to the method described in Naumyn-Schmiederberg's Arch. Pharmacol., 2001, 363, 429-438, is aimed at determining the affinity of compounds of the present invention for muscarinic receptors.

Membranes (250 μg/ml) of rat brain are incubated (2 hours, 20° C.) in the presence of a series of concentrations (0.01-10 μM) of each compound of the invention (diluted starting from a 10 mM stock solution in DMSO) and [$^3$H]-oxotremorine-M (S.A.: 3174 GBq/mmol: 2 nNM) in phosphate buffer (NaH$_2$PO$_4$ 20 mM, pH 7.4); final volume: 250 μl. The specific binding is determined by incubating membranes in the presence of atropine (1 μM). The affinity of the compounds of the present invention for muscarinic receptors is characterised by determination of the $K_i$.

The results show that, up to a concentration of 10 μM, all of the compounds of the present invention have no affinity for muscarinic receptors ($K_i$>10$^{-5}$M).

EXAMPLE D

Displacement of Binding of [$^{125}$I]-α-bungarotoxin on "Type α7" Nicotinic Receptors of Rat Brain This study, carried out according to the method described in Molec. Pharmacol., 1986, 30; 427-436, is aimed at determining the affinity of compounds of the present invention for type α7 central nicotinic receptors.

Membranes (1000 μg/ml) of rat brain are incubated (5 hours, 37° C.) in the presence of a series of concentrations (0.01-10 μM) of each compound of the present invention (diluted starting from a 10 mM stock solution in DMSO) and [$^{125}$I]-α-bungarotoxin (S.A.: 7.4 TBq/mmol: 1 nM) in Krebs buffer (Tris-HCl 50 mM, KCl 5 mM, MgCl$_2$ 1 mM, CaCl$_2$ 2 mM, NaCl 100 mM, pH 7.4) with 0.05% BSA; final volume: 500 μl. The non-specific binding is determined by incubating membranes in the presence of α-bungarotoxin (1 μM). The affinity of compounds of the present invention for type CC7 nicotinic receptors is characterised by determination of the $K_i$.

The results indicate that, up to a concentration of 10 μM, all of the compounds of the present invention have no affinity for type α7 central nicotinic receptors ($K_i > 10^{-5}$M).

EXAMPLE E

Displacement of Binding of [$^3$H]-cytisine on "Type α4β2" Nicotinic Receptors of Rat Brain This study, carried out according to the technique described in Molec. Pharmacol., 1990, 39; 9-12, is aimed at determining the affinity of compounds of the present invention for type α4β2 central nicotinic receptors.

Membranes (250 μg/ml) of rat brain are incubated (2 hours, 20° C.) in the presence of a series of concentrations (0.01-10 μM) of each compound of the present invention (diluted starting from a 10 mM stock solution in DMSO) and [$^3$H]-cytisine (S.A.: 1184 GBq/mmol: 2 nM) in phosphate buffer (NaH$_2$PO$_4$ 20 mM, pH 7.4); final volume: 250 μl. The non-specific binding is determined by incubating membranes in the presence of 10 μM of (−)nicotine. The affinity of the compounds of the present invention for type α4β2 central nicotinic receptors is characterised by determination of the $K_i$.

The results obtained show that the compounds of the present invention have a strong affinity for type αβ12 central nicotinic receptors. Thus, Example 2 has a $K_i$ of $6.9 \times 10^{-8}$M.

These results, and also those obtained in Examples A to D, indicate that the compounds of the present invention are powerful central nicotinic ligands that are specific to type α4β2 receptors.

EXAMPLE F

In Vivo Measurement of the Release of Acetylcholine by Means of Intra-cortical Microdialysis in the Conscious Wistar Rat The systemic administration of nicotine and nicotinic agonists causes an increase, in vivo, of acetylcholine in various regions of the brain (Neurochem. Res., 1996, 21, 1181-1186; Eur. J. Pharmacol., 1998, 351, 181-188; Br. J. Pharmacol., 1999, 127, 1486-1494). A microdialysis probe is implanted in the median prefrontal cortex of male Wistar rats. Six or seven days after they have been implanted, the probes are perfused with Ringer's solution (NaCl 147 mM, KCl 2.7 mM, CaCl$_2$ 1.2 mM, MgCl$_2$ 1 mM, neostigmine 20 nM) at a flow rate of 1 μl/min, the animal being free to move. After 2 hours in the animal quarters, the product under test is administered by the intraperitoneal route. A group of control animals receives the solvent used for the product. The dialysates (30 μl) are then collected every 30 minutes for 4 hours in order to measure the cortical extra-synaptic concentrations of acetylcholine by means of HPLC with amperometric detection. The results are expressed in pg of acetylcholine/dialysate, and inter-group comparisons are carried out by means of analysis of variance using 2 factors (treatment×time), with measurements being repeated over time.

The results obtained show that the compounds of the present invention increase, in vivo, the cortical release of acetylcholine in a dose-dependent manner for doses ranging from 1 to 10 mg/kg IP, indicating the α4β2-agonist character of the compounds of the present invention. Thus, Example 2, one hour after administration at a dose of 3 mg/km IP, induces an increase of +86% in the release of acetylcholine in the prefrontal cortex of the conscious Wistar rat.

EXAMPLE G

Abdominal Contractions Induced by Phenyl-p-benzoquinone (PBQ) in the NMRI Mouse

Intraperitoneal administration of an alcoholic solution of PBQ causes abdominal cramps in the mouse (Proc. Soc. Exp. Biol., 1957, 95, 729-731). The cramps are characterised by repeated contractions of the abdominal musculature, accompanied by extension of the hind limbs. Most analgesics antagonise these abdominal cramps (Brit. J. Pharmacol. Chem., 1968, 32, 295-310). At t=0 min., the animals are weighed and the compound being studied is administered by the IP route. A group of control animals is given the solvent used for the compound. At t=30 min., an alcoholic solution of PBQ (0.2%) is administered by the IP route in a volume of 0.25 ml/mouse. Immediately after administration of the PBQ, the animals are placed in cylinders of plexiglass (L=19.5 cm; I.D.=5 cm). From t=35 min. to t=45 min., the animals' reaction is observed and the experimenter notes the total number of abdominal cramps per animal. The results are expressed as the percentage inhibition of the number of abdominal cramps measured in the control animals, at the active dose of the compound studied.

The results obtained show inhibition of the order of 70% for active doses of 10 mg/kg IP, which demonstrates that the compounds of the invention possess antalgic properties. Thus, Example 15, administered at a dose of 10 mg/kg IP, reduces (−69%) the number of abdominal cramps caused by the administration of PBQ to the mouse.

EXAMPLE H

Social Recognition in the Wistar Rat

Initially described in 1982 (J. Comp. Physiol., 1982, 96, 1000-1006), the social recognition test has subsequently been proposed by various authors (Psychopharmacology, 1987, 91, 363-368; Psychopharmacology, 1989, 97, 262-268) for studying the mnemocognitive effects of new compounds. The test is based on the natural expression of the olfactory memory of the rat and its natural tendency to forget and allows evaluation of memorisation, by recognition of a young congeneric animal, by an adult rat. A young rat (21 days), taken at random, is placed for 5 minutes in the cage housing an adult rat. With the aid of a video device, the experimenter observes the social recognition behaviour of the adult rat and measures its overall duration. The young rat is then removed from the adult rat's cage and is placed in its own cage until the second introduction. The adult rat is given the compound under test by the intraperitoneal route and, after 2 hours, is again brought into the presence (5 minutes) of the young rat. The social recognition behaviour is then observed again and its duration measured. The assessment criterion is the difference (T2−T1), expressed in seconds, between the "recognition" times of the 2 encounters.

The results obtained show a difference (T2−T1) ranging from −22 s to −38 s for doses ranging from 1 to 10 mg/kg IP, which shows that the compounds of the invention very greatly enhance memorisation, even at a low dose. Thus, Example 2, at a dose of 10 mg/kg IP, induces a difference (T2−T1) of 38 s.

EXAMPLE I

Pharmaceutical Compositions for 1000 Tablets
Each Containing 10 mg of Active Ingredient

| | |
|---|---|
| Compound of Example 2 | 10 g |
| Hydroxypropyl methyl cellulose | 10 g |
| Wheat starch | 15 g |
| Lactose | 90 g |
| Magnesium stearate | 2 g |

The invention claimed is:

1. A compound selected from those of formula (I):

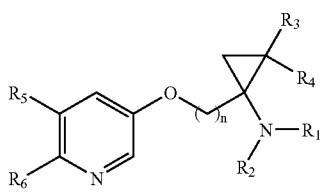

(I)

wherein:

n represents an integer from 1 to 6 inclusive, $R_1$ and $R_2$, which may be identical or different, each independently of the other represent a hydrogen atom, a linear or branched ($C_1$-$C_6$)alkyl group or an aryl-($C_1$-$C_6$)alkyl group in which the alkyl moiety may be linear or branched, $R_3$ and $R_4$, which may be identical or different, each independently of the other represent a hydrogen atom or a linear or branched ($C_1$-$C_6$)alkyl group, wherein at least one of the two groups $R_3$ or $R_4$ represents a linear or branched ($C_1$-$C_6$)alkyl group, $R_5$ and $R_6$, which may be identical or different, each independently of the other represent a hydrogen atom or a linear or branched ($C_1$-$C_6$)alkyl, halogen, hydroxy, linear or branched ($C_1$-$C_6$)alkoxy, cyano, nitro, linear or branched ($C_2$-$C_6$)acyl, linear or branched ($C_1$-$C_6$)alkoxycarbonyl, linear or branched ($C_1$-$C_6$)trihaloalkyl or linear or branched ($C_1$-$C_6$)trihaloalkoxy group or an amino group optionally substituted by one or two linear or branched ($C_1$-$C_6$)alkyl groups, it being understood that an aryl group means phenyl, biphenyl, naphthyl, dihydronaphthyl, tetrahydronaphthyl, indanyl or indenyl group, each of the groups being optionally substituted by one or more identical or different groups selected from halogen, linear or branched ($C_1$-$C_6$)alkyl, hydroxy, cyano, nitro, linear or branched ($C_1$-$C_6$)alkoxy, linear or branched ($C_2$-$C_7$)acyl, linear or branched ($C_1$-$C_6$) alkoxycarbonyl, linear or branched ($C_1$-$C_6$)trihaloalkyl and linear or branched ($C_1$-$C_6$)trihaloalkoxy groups and amino groups optionally substituted by one or two linear or branched ($C_1$-$C_6$)alkyl groups, its enantiomers, diastereoisomers and additional salts thereof with a pharmaceutically acceptable acid or base.

2. The compound of claim 1, wherein n is an integer having the value 1, its enantiomers, diastereoisomers, and addition salts thereof with a pharmaceutically acceptable acid or base.

3. The compound of claim 1, wherein $R_1$ and $R_2$, which may be identical or different, each represent a hydrogen atom or a linear or branched ($C_1$-$C_6$)alkyl group, its enantiomers, diastereoisomers, and addition salts thereof with a pharmaceutically acceptable acid or base.

4. The compound of claim 1, wherein $R_3$ and $R_4$, which may be identical or different, each represent a hydrogen atom or methyl group, its enantiomers, diastereoisomers, and addition salts thereof with a pharmaceutically acceptable acid or base.

5. The compound of claim 1, wherein $R_5$ and $R_6$, which may be identical or different, each represents a hydrogen atom or a halogen atom, its enantiomers, diastereoisomers, and addition salts thereof with a pharmaceutically acceptable acid or base.

6. The compound of claim 1 which is selected from:
 (1S,2S), (1R,2R)-N,2-dimethyl-1-[(3-pyridinyloxy)methyl]cyclopropanamine,
 (1S,2S)- or (1R,2R)-(−)-N,2-dimethyl-1-[(3-pyridinyloxy)methyl]cyclopropanamine,
 (1S,2S)- or (1R,2R)-(+)-N,2-dimethyl-1-[(3-pyridinyloxy)methyl]cyclopropanamine,
 (1S,2S), (1R,2R)-2-methyl-1-[(3-pyridinyloxy)methyl]cyclopropanamine,
 (1S,2S)- or (1R,2R)-(−)-2-methyl-1-[(3-pyridinyloxy)methyl]cyclopropanamine,
 (1S,2S)- or (1R,2R)-(+)-2-methyl-1-[(3-pyridinyloxy)methyl]cyclopropanamine,
 (1S,2S), (1R,2R)-N,N,2-trimethyl-1-[(3-pyridinyloxy)methyl]cyclopropanamine,
 (1S,2S)- or (1R,2R)-(+)-N,N,2-trimethyl-1-[(3-pyridinyloxy)methyl]cyclopropanamine,
 (1S,2S)- or (1R,2R)-(−)-N,N,2-trimethyl-1-[(3-pyridinyloxy)methyl]cyclopropanamine,
 (1S,2S), (1R,2R)-1-{[(6-chloro-3-pyridinyl)oxy]methyl}-N,2-dimethylcyclopropanamine,
 (1S,2S)- or (1R,2R)-(−)-1-{[(6-chloro-3-pyridinyl)oxy]methyl}-N,2-dimethylcyclopropanamine,
 (1S,2S)- or (1R,2R)-(+)-1-{[(6-chloro-3-pyridinyl)oxy]methyl}-N,2-dimethylcyclopropanamine,
 (1S,2S), (1R,2R)-1-{[(6-chloro-3-pyridinyl)oxy]methyl}-2-methylcyclopropanamine,
 (1S,2S)- or (1R,2R)-(−)-1-{[(6-chloro-3-pyridinyl)oxy]methyl}-2-methylcyclopropanamine,
 (1S,2S)- or (1R,2R)-(+)-1-{[(6-chloro-3-pyridinyl)oxy]methyl}-2-methylcyclopropanamine,
 (1S,2S), (1R,2R)-1-{[(6-chloro-3-pyridinyl)oxy]methyl}-N,N,2-trimethylcyclopropanamine,
 (1S,2S)- or (1R,2R)-(+)-1-{[(6-chloro-3-pyridinyl)oxy]methyl}-N,N,2-trimethylcyclopropanamine,
 (1S,2S)- or (1R,2R)-(−)-1-{[(6-chloro-3-pyridinyl)oxy]methyl}-N,N,2-trimethylcyclopropanamine,
 (1S,2R), (1R,2S)-N,2-dimethyl-1-[(3-pyridinyloxy)methyl]cyclopropanamine,
 (1S,2R)- or (1R,2S)-(+)-N,2-dimethyl-1-[(3-pyridinyloxy)methyl]cyclopropanamine,
 (1S,2R)- or (1R,2S)-(−)-N,2-dimethyl-1-[(3-pyridinyloxy)methyl]cyclopropanamine,
 (1S,2R), (1R,2S)-1-{[(5-bromo-3-pyridinyl)oxy]methyl}-N,2-dimethylcyclopropanamine,
 (1S,2R), (1R,2S)-2-methyl-1-[(3-pyridinyloxy)methyl]cyclopropanamine,
 (1S,2R), (1R,2S)-N,N,2-trimethyl-1-[(3-pyridinyloxy)methyl]cyclopropanamine,
 (R,S)-N,2,2-trimethyl-1-[(3-pyridinyloxy)methyl]cyclopropanamine, (R or S)-(+)-N,2,2-trimethyl-1-[(3-pyridinyloxy)methyl]
    cyclopropanamine, and
(R or S)-(−)-N,2,2-trimethyl-1-[(3-pyridinyloxy)methyl]
    cyclopropanamine,
its enantiomers, diastereoisomers, and addition salts thereof with a pharmaceutically acceptable acid or base.

7. A pharmaceutical composition comprising as active ingredient a compound according to claim 1, alone or in combination with one or more pharmaceutically acceptable, inert, non-toxic excipients or carriers.

* * * * *